US012419591B2

(12) United States Patent
Xu et al.

(10) Patent No.: US 12,419,591 B2
(45) Date of Patent: Sep. 23, 2025

(54) SPECTRALLY AND SPATIALLY RESOLVED X-RAY AND PARTICLE DETECTION SYSTEM

(71) Applicant: Carl Zeiss X-ray Microscopy, Inc., Dublin, CA (US)

(72) Inventors: Xiaochao Xu, Pleasanton, CA (US); Christoph Graf Vom Hagen, Schwaebisch Gmuend (DE)

(73) Assignee: CARL ZEISS X-RAY MICROSCOPY, INC., Dublin, CA (US)

(*) Notice: Subject to any disclaimer, the term of this patent is extended or adjusted under 35 U.S.C. 154(b) by 473 days.

(21) Appl. No.: 17/919,646

(22) PCT Filed: Apr. 24, 2020

(86) PCT No.: PCT/US2020/029679
§ 371 (c)(1),
(2) Date: Oct. 18, 2022

(87) PCT Pub. No.: WO2021/216075
PCT Pub. Date: Oct. 28, 2021

(65) Prior Publication Data
US 2023/0165541 A1    Jun. 1, 2023

(51) Int. Cl.
*A61B 6/03*    (2006.01)
*A61B 6/42*    (2024.01)
*A61B 6/58*    (2024.01)

(52) U.S. Cl.
CPC ............ *A61B 6/032* (2013.01); *A61B 6/4208* (2013.01); *A61B 6/582* (2013.01)

(58) Field of Classification Search
CPC ........ A61B 6/032; A61B 6/4208; A61B 6/582
See application file for complete search history.

(56) References Cited

U.S. PATENT DOCUMENTS

| 5,847,499 A | 12/1998 | Rieppo et al. |
| 12,130,392 B2 * | 10/2024 | Xu .................. G02F 1/1354 |
| 2016/0216384 A1 | 7/2016 | Chen et al. |

FOREIGN PATENT DOCUMENTS

| CN | 102243318 A | 11/2011 |
| CN | 108449982 A | 8/2018 |

(Continued)

OTHER PUBLICATIONS

International Search Report and Written Opinion of the International Searching Authority, mailed on Dec. 11, 2020, from International Application No. PCT/US2020/029679, filed on Apr. 24, 2020. 15 pages.

(Continued)

*Primary Examiner* — Nicole M Ippolito
(74) *Attorney, Agent, or Firm* — HoustonHogle LLP

(57) ABSTRACT

A detection system for an x-ray or charged particle imaging system utilizes high bandgap, direct conversion x-ray detection materials. The signal of the x-ray/charged particle projection is recorded in a spatial light modulator such as a liquid crystal (LC) light valve. The light valve is then read-out by a polarized light optical microscope and a high speed camera. The camera is used to track the blooming spots in the light valve to resolve their intensity, and relate that intensity of the input x-ray photon or charged particle. This allows of spatially resolved, imaging, x-ray and/or charged particle spectrometer.

16 Claims, 14 Drawing Sheets

(56) References Cited

FOREIGN PATENT DOCUMENTS

| CN | 109342350 A | 2/2019 |
|---|---|---|
| CN | 113169014 A | 7/2021 |
| WO | WO 2020/097111 A1 | 5/2020 |

OTHER PUBLICATIONS

CN first Office Action, mailed Jan. 8, 2025 from Chinese Patent Application No. 202080100153.7, filed Apr. 24, 2020. 21 pages.

* cited by examiner

SPECTRALLY AND SPATIALLY RESOLVED X-RAY AND PARTICLE DETECTION SYSTEM

RELATED APPLICATIONS

This application is a § 371 National Phase Application of International Application No. PCT/US2020/029679, filed on Apr. 24, 2020, now International Publication No. WO 2021/216075 A1, published on Oct. 28, 2021, which is incorporated herein by reference in its entirety.

BACKGROUND OF THE INVENTION

X-ray microscopy and other x-ray imaging applications require the detection of x-ray photons (<500 keV) with high spatial resolution and high efficiency. This can generally be achieved with a scanning system and a simple (e.g., single element) detection system or achieved with a full-field and a more complex detection system that is pixelated or spatially resolved.

The detection systems of some current full-field x-ray microscopes utilize optical coupling of a thin scintillator detector to a charge coupled device (CCD) or complementary metal oxide semiconductor (CMOS) camera. Sometimes the coupling is direct. In other cases, they are coupled via an optical microscope. These setups enable high-resolution imaging by combining magnification in the x-ray regime and/or in the optical regime.

Another class of full-field detection systems utilize high bandgap, direct conversion photoconductive detection materials. The signal of the x-ray or high energy particle, for example, projection is recorded in an adjoining spatial light modulator, such as a liquid crystal (LC) light valve. The light valve is then illuminated by an external light source of an optical microscope for example. This configuration can mitigate the loss of light in the optical system over the current scintillator-optical microscope-camera detection systems.

Spectrally/energy-resolving detection systems are also known. Current high-resolution x-ray (also including γ-ray/charged-particle) spectrometers normally consist of a semiconductor (for example, silicon, high-purity germanium at liquid nitrogen temperatures and CdTe/CdZnTe) detector and the accompanying electronics to amplify and process the electrical pulses formed by the impacting individual x-ray photons or particles. Most common ones have only one detector element and therefore only detect the energy and timing information of the incoming x-ray photons.

Pixelated spectrally-resolving detection systems are also known. Commonly, they have repeated identical amplifiers and processing circuits to provide spatial resolution. Such systems, however, generally have lower energy resolution due to the smaller pixels. And, the cost of these pixelated detectors is usually high because the semiconductor processing procedures and high costs of the electronics. A recent development in spatially resolving spectrometer is pnCCD x-ray camera, which provides both high energy and spatial (48 micrometer (μm) pixels) resolution. However, since it can only be made from silicon for now, its applicable detection energies are limited to lower x-ray energies.

A common drawback for all the existing spectrometers is that they can only be used to detect relatively low x-ray photon fluxes. This is because all these detectors need to measure the x-ray photons individually to detect their energies (and positions for spatially resolved ones). Each x-ray photon induces an electronic pulse in the detector and the pulses are measured individually. Higher flux rates thus cause the electronic pulses to overlap each other, therefore leading to pileup problem, which limits the maximum possible flux rate.

For the existing spectrometers (mostly spatially-resolved ones), one way to overcome this problem is to reduce the pixel size. However, there are both physical and technological limits to this strategy. Physically small pixels will have larger crosstalk due to coupling of pixels and more importantly, the weighting potential crosstalk, i.e. the x-ray deposit within one pixel region induces signals at multiple neighboring pixels. Therefore, one quickly reaches the limit where smaller pixels will not significantly reduce the count numbers. Technologically, smaller pixels are also limited by the processing technologies and associated costs.

SUMMARY OF THE INVENTION

The disclosed embodiments concern spectrometers and particularly spatially-resolved particle (e.g., x-ray or charged particle) spectrometers. The present approach optically measures and counts the x-ray photons or other particles, typically in a much smaller area. Therefore, they can detect at higher rates and higher spatial resolution.

In more detail, in one example, a liquid crystal light valve spatial light modulator is coupled with a high-resolution microscope objective. A high speed camera is then used to resolve x-ray or particle interaction events in a very small area. Although the readout of the camera might not be fast, due to the fact of the small area, even when the flux rate is high, the rate of events impacting individual pixels or regions is low. Therefore, such a setup can detect at a higher flux rate than current x-ray spectrometers. Also with high-resolution detection, spatial resolution can be very high. In addition, there are wide range of choices for the direct-conversion detector materials, and those materials can be tailored for detecting higher energies and/or higher resolution as required by the particular use-case.

The present detection systems and associated imaging systems employ a photoconductive x-ray detector that has a sandwich structure comprised of direct conversion x-ray detection photoconductor layer and a spatial light modulator such as a liquid crystal (LC) light valve, in combination with a high speed camera. During operation, x-ray photons will then generate electron-hole pairs in the photoconductor layer and thus locally modify the electrical field. This local field will create a local reorientation of the liquid crystals in the adjacent LC film that will appear as spots. Over time, these spots will exhibit a blooming effect: growing and then dissipating. By tracking the blooming over time using the camera, both the location and the energy of the incident photon/particle can be determined, yielding both spectral and spatial resolution.

In general, according to one aspect, the invention features a spectrally and spatially resolved particle detection system. The system comprising a photoconductive detector, an optical microscope for reading out the photoconductive detector, and a camera coupled to the photoconductive detector by the optical microscope. A computer system, (e.g., special purpose computer such as a graphic processing unit (GPU), application specific integrated circuit (ASIC), field programmable array (FPGA), general purpose computer or some combination of these or other computer systems) is then used that obtains the images generated by the camera and tracks the response of the photoconductive detector to particles over time.

Typically, the computer system tracks blooming in the photoconductive detector induced by the particles to resolve locations on the photoconductive detector and energy of the particles.

Usually, the computer system determines the energy of the particles by reference to an energy/intensity map that relates a maximum spot intensity or integrated spot intensity, or a fit to the intensity map to an energy of the received particle.

Typically, an interval between successive frames captured by the camera is less than a relaxation time of the photoconductive detector. This way, the blooming of spots on the photoconductive detector can be tracked in order to resolve their location and intensity.

As a consequence, for many applications, the camera will be a high speed camera. For example, an interval between successive frames captured by the camera is less than 1 millisecond, in many implementations.

In one use, the photoconductive detector is used to detect x-rays.

In a current embodiment, the photoconductive x-ray detector comprises a liquid crystal light valve and photoconductive detector layer. This photoconductive detector layer might comprise bismuth, lead, mercury, tellurium, selenium, or thallium. Moreover, the optical microscope can be a polarization light microscope that reads-out the photoconductive detector in transmission or reflection.

In general, according to another aspect, the invention features a particle detection method, comprising converting particles into electron-hole pairs in a photoconductive detector, reading out the photoconductive detector with a camera coupled to the photoconductive detector; and processing images generated by the camera and tracking the response of the photoconductive detector to particles over time to determine the position and the energy of the particles.

The image processing is performed in a computer system such as a special purpose computer such as a graphic processing unit (GPU), application specific integrated circuit (ASIC), field programmable array (FPGA), general purpose computer or some combination of these or other computer systems. The computer system could even be a part of the camera.

In general, according to another aspect, the invention features an imaging system. This system comprises an object stage system for holding an object, a photoconductive detector for detecting particles from the object, and a camera coupled to the photoconductive detector by the optical microscope. A computer system then obtains the images generated by the camera and tracks the response of the photoconductive detector to particles over time to image the object and determine an energy of the particles.

In general, according to still another aspect, the invention features a method for calibrating a particle detection system. The method comprises generating particles of known energy, converting particles into electron-hole pairs in a photoconductive detector, reading out the photoconductive detector with a camera, and processing images generated by the camera and tracking spots generated by the particles received by the photoconductive detector and determining a relationship between the spots and the energy of the particles.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1A:
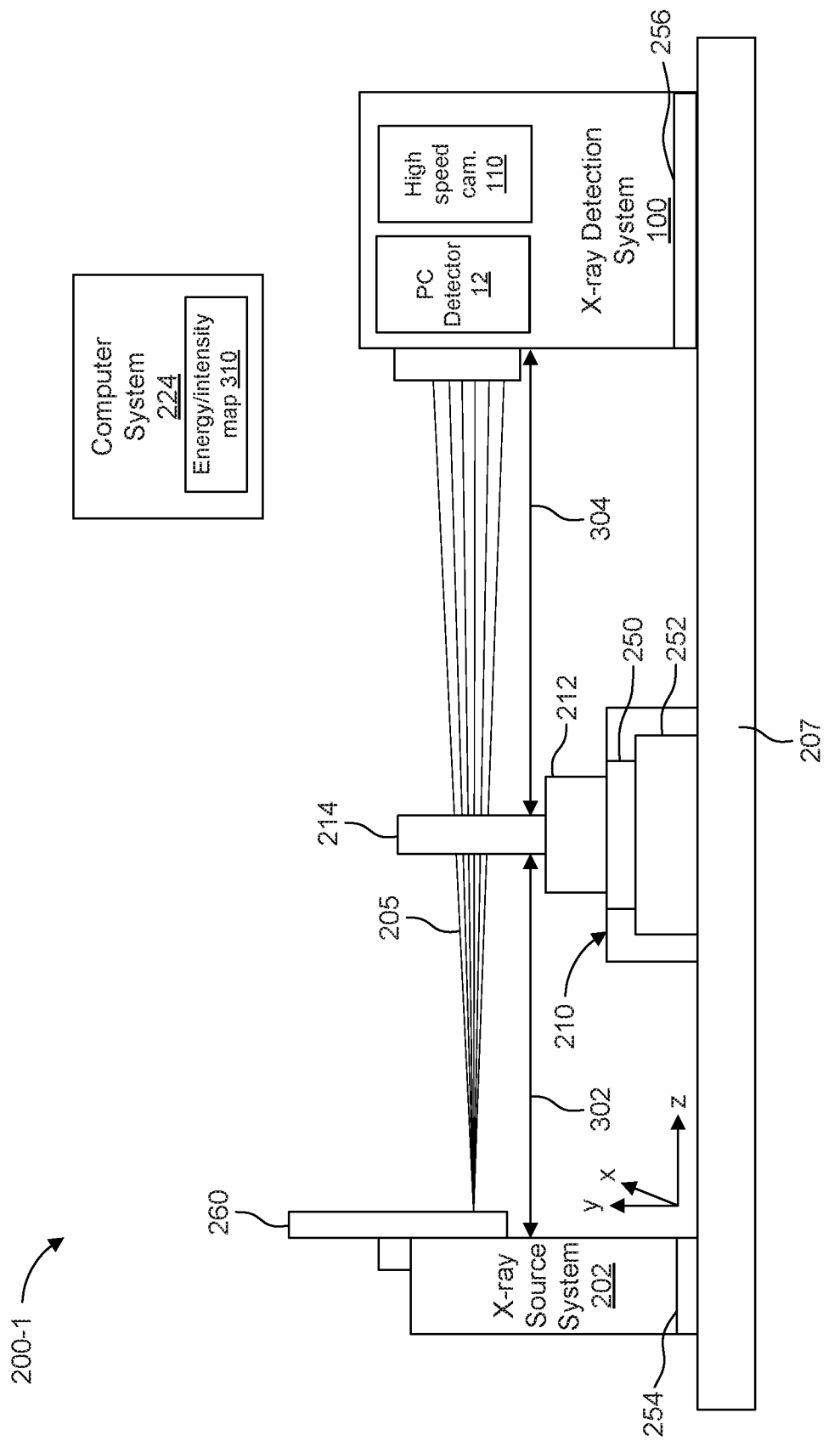
FIG. 1A is a schematic diagram of an x-ray microscope employing a detection system according to the present invention.

FIG. 1A is a schematic diagram of an X-ray CT microscopy system 200-1 to which the spectrally and spatially resolved x-ray detection systems 100 is applicable.

Nevertheless, the present invention is also applicable to the detection of other particles including charged particle analysis systems and non-microscopy systems.

The microscope 200-1 generally includes an X-ray imaging system that has an X-ray source system 202 that generates a polychromatic or possibly monochromatic X-ray beam 205 and an object stage system 210 with object holder 212 for holding an object 214 and positioning it to enable scanning of the object 214 in the stationary beam 205. The x-ray detection system 100 detects the beam 205 after it has been modulated by the object 214. A base such as a platform or optics table 207 provides a stable foundation for the microscope 200-1.

In general, the object stage system 210 has the ability to position and rotate the object 214 in the beam 205. Thus, the object stage system 210 will typically include a precision 3-axis stage 250 that translates and positions the object along the x, y, and z axes, very precisely but over relatively small ranges of travel. This allows a region of interest of the object 214 to be located within the beam 205. The 3-stage 250 is mounted on a theta stage 252 that rotates the object 214 in the beam around the y-axis. The theta stage 252 is in turn mounted on the base 107.

The source system 202 will typically be either a synchrotron x-ray radiation source or alternatively a "laboratory x-ray source" in some embodiments. As used herein, a "laboratory x-ray source" is any suitable source of x-rays that is not a synchrotron x-ray radiation source. Laboratory x-ray source 202 can be an X-ray tube, in which electrons are accelerated in a vacuum by an electric field and shot into a target piece of metal, with x-rays being emitted as the electrons decelerate in the metal. Typically, such sources produce a continuous spectrum of background x-rays combined with sharp peaks in intensity at certain energies that derive from the characteristic lines of the selected target, depending on the type of metal target used. Furthermore, the x-ray beams are divergent and lack spatial and temporal coherence.

In one example, source 202 is a rotating anode type or microfocused source, with a Tungsten target. Targets that include Molybdenum, Gold, Platinum, Silver or Copper also can be employed. Preferably a transmission configuration is used in which the electron beam strikes the thin target from its backside. The x-rays emitted from the other side of the target are used as the beam 205.

The x-ray beam generated by source 202 is preferably conditioned to suppress unwanted energies or wavelengths of radiation. For example, undesired wavelengths present in the beam are eliminated or attenuated, using, for instance, energy filters (designed to select a desired x-ray wavelength range (bandwidth)) held in a filter wheel 260. Conditioning is also often provided by collimators or condensers and/or an x-ray lens such as a zone plate lens.

When the object 214 is exposed to the X-ray beam 205, the X-ray photons transmitted through the object form a modulated x-ray beam that is received by the detection system 100. In some other examples, a zone plate objective x-ray lens is used to form an image onto x-ray detection system 100.

Typically, a magnified projection image of the object 214 is formed on the detection system 100. The magnification is equal to the inverse ratio of the source-to-object distance 302 and the source-to-detector distance 304.

The x-ray source system 202 and the detection system 100 are sometimes mounted on respective z-axis stages. For example, in the illustrated example, the x-ray source system 202 is mounted to the base 207 via a source stage 254, and the detection system 100 is mounted to the base 207 via a detector stage 256. In practice, the source stage 254 and the detector stage 256 are lower precision, high travel range stages that allow the x-ray source system 202 and detection system 100 to be moved into position, often very close to the object during object scanning and then be retracted to allow the object to be removed from, a new object to be loaded onto, and/or the object to be repositioned on the object stage system 210.

According to the invention, the detection system 100 generally comprises photoconductive x-ray detector 12 and a camera 110. The camera is often a high speed camera in the sense that it captures images at a rate that is fast enough to resolve the blooming induced in the photoconductive x-ray detector 12 associated with the detection of individual x-ray photons or other particles. As a result, the camera will typically capture images at greater than 60 frames a second. It preferably has a speed of equal to or greater than 120 frames per second as is preferably faster than 500 or even a 1000 frames per second.

The operation of the system 200-1 and the scanning of the object 214 is controlled by a computer system 224 that often includes an image processor subsystem and a controller subsystem. The computer system is used to set bias voltages of the photoconductive x-ray detector 12 and to readout the optical images detected by the camera 110 of the detection system 100.

According to the invention, the computer system 224 obtains the images generated by the camera 110 and tracks blooming spots induced by the x-ray photons or other particles detected in the photoconductive x-ray detector 12 over time, both the location on the photoconductive x-ray detector 12 and the energy of the photons can be determined, yielding both spectral and spatial resolution.

Specifically, the computer system 224 determines the energy of the photons or other particles by reference to an energy/intensity map 310 such as a lookup table (LUT). This map relates the maximum spot intensity or integrated spot intensity, or a fit to the intensity map to the energy of the received particle.

It should be noted that the computer system need not be a unitary device. For example a single-board computer or microcontroller might be used to as the control system for the microscopy system 200-1. A separate computer might be used to process the images generated by the camera to generate the spatially and spectrally resolved object images or projections of the object and/or perform tomographic reconstruction of the object based on the various projections. In fact, the camera images might be stored and then later processed or reprocess in order to generate the object images and reconstructions. As a result, a special purpose computer such as a graphic processing unit (GPU), application specific integrated circuit (ASIC), field programmable array (FPGA), general purpose computer or some combination of these or other compute systems would be included as part of the computer system 224 to process the images. In addition, these compute systems could also be integrated within the housing of the camera 110.

For the reconstructions, an image processor of the computer system combines the projection images of the object using a CT reconstruction algorithm to create 3D tomographic volume information for the object. The reconstruction algorithm may be analytical, where convolution or frequency domain filtering of the projection data is combined with back projection onto a reconstruction grid. Alternatively, it may be iterative, where techniques from numerical linear algebra or optimization theory are used to solve a discretized version of the projection process, which may include modeling of the physical properties of the imaging system.

Figure 1B:
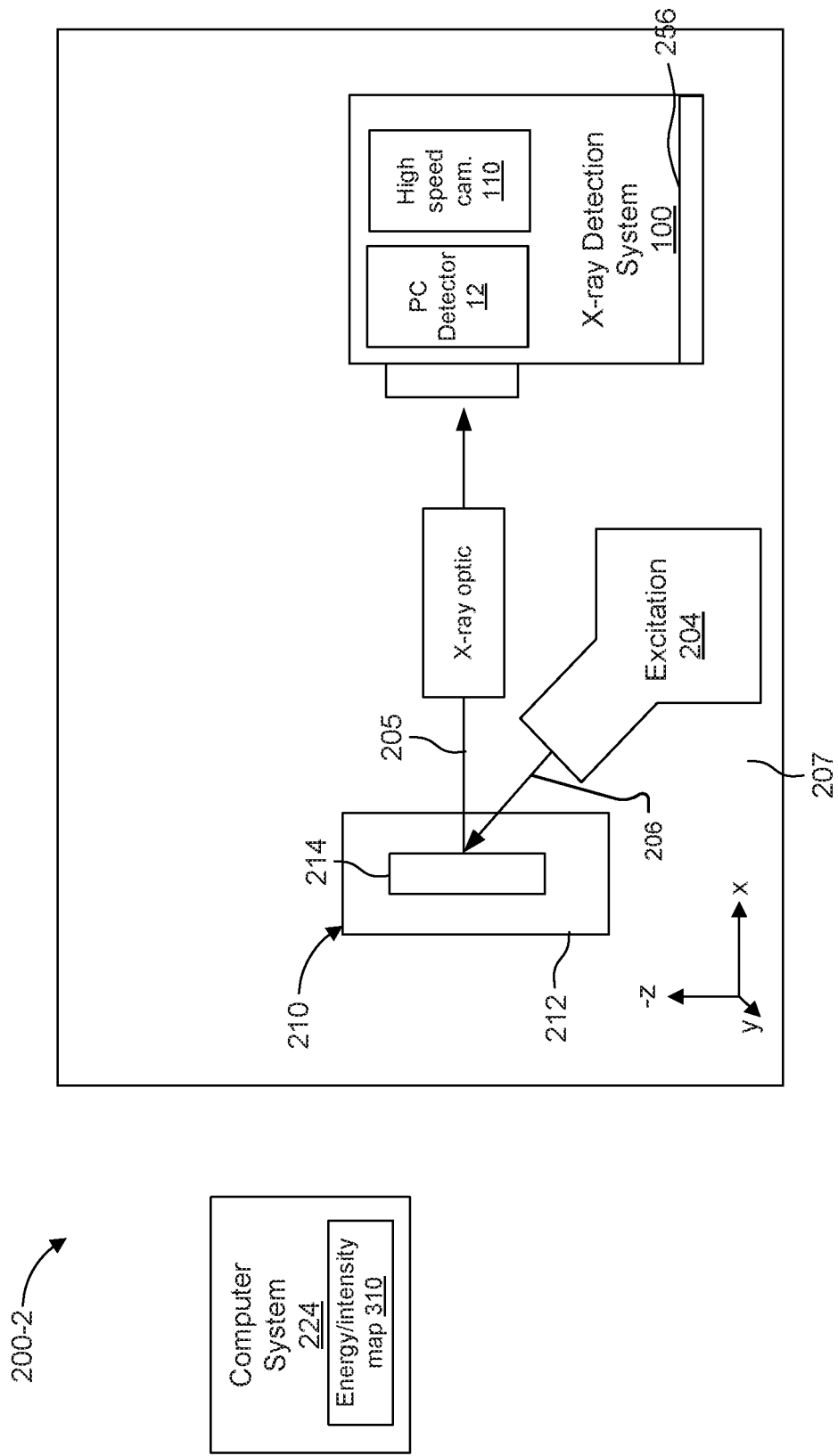
FIG. 1B is a schematic diagram of an x-ray fluorescence (XRF) microscope employing a detection system according to the present invention.

FIG. 1B is a schematic diagram of an X-ray fluorescence XRF microscopy system 200-2 to which the spectrally and spatially resolved x-ray detection systems 100 is also applicable.

The XRF microscope 200-2 generally includes an X-ray imaging system that has an excitation system 204 that generates high energy beam 206 to induce x-ray fluorescence in elements of the object 214. This beam 206 might be an x-ray beam or an electron beam, for example.

Often, an x-ray optic such as an objective lens or reflective element, e.g., polycapillary optic or Kumakhov-lenses, is used to capture the fluorescence x-rays from the object and form an image on the detection system.

Here, the object stage system 210 has the ability to position and rotate the object 214 in the excitation beam 206. Thus, the object stage system 210 will also typically include a precision three (3) or more axis stage that translates and positions the object.

Figure 2:
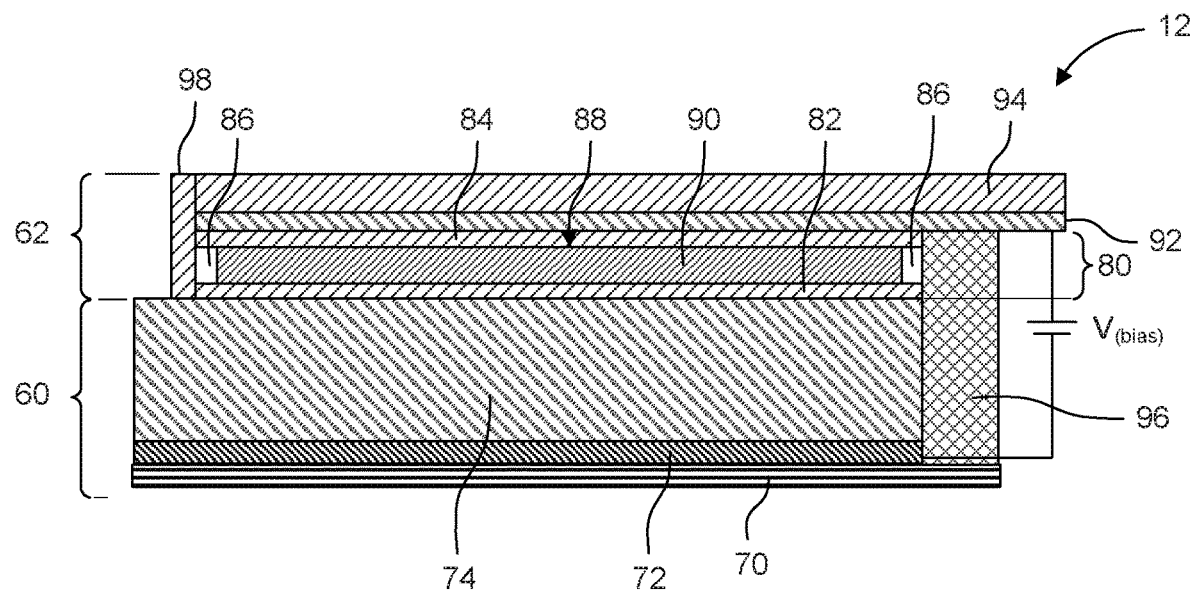
FIG. 2 is a side cross-sectional view of a photoconductive x-ray detector.

FIG. 2 shows the basic setup of one possible photoconductive detector 12 that could be used in an implementation of the present invention. The detector is typically used to detector x-rays and other particles, including charged particles. It comprises an electro-optic spatial light modulator such as an LC light valve 62 disposed on one side of a photoconductive assembly 60.

The photoconductive assembly 60 includes a glass substrate 70 having a transparent, conductive Indium Tin Oxide (ITO) electrode 72 thereon, and a photoconductor layer 74 having a thickness in the range of about 5 to 2000 μm.

The electro-optic light modulator 62 includes a liquid crystal (LC) cell 80. The LC cell 80 includes a pair of alignment layers 82 and 84. Spacers 86 act between the alignment layers maintain a uniform separation between the alignment layers 82 and 84 and thus define an LC cavity 88.

The nematic liquid crystal material 90 fills the LC cavity 88. A top ITO electrode 92 overlies the alignment layer 84 while a glass substrate 94 overlies the ITO electrode 92. The ITO electrode 92 and the glass substrate 94 overhang the photoconductive assembly 60 to facilitate connection of a potential source V(bias) between the ITO electrodes 92 and 72 respectively.

The LC cell 80 is constructed in a similar manner to self-standing LC cells with the exception that the LC cell is defined by glass substrate 94 and the photoconductor layer 74 as opposed to a pair of glass substrates.

Epoxy 96 extends between the ITO electrodes 92 and 72 to fill areas between the ITO electrodes separated by air and inhibit breakdown of the LC cell 80 when a potential is placed across the ITO electrodes. Epoxy 96 also seals the electro-optic light modulator 58 to inhibit separation of the layers forming the photoconductive x-ray detector 12.

In the past, most have used amorphous selenium (a-Se) as the photoconductor layer 74. On the other hand, the photoconductor layer 74 is fabricated from a material that has both a high-bandgap and high electrical resistivity. The advantage of high-bandgap photoconductors is that they normally produce a much smaller leaking current under a high-voltage bias. This is important in reducing the detector noise. In addition, it will simplify and stabilize the performance of the LC light valve. It also simplifies the analysis and modelling of the detector system.

For example, the photoconductor layer 74 might be monocrystalline bismuth silicon oxide $Bi_{12}SiO_{20}$ (BSO) or (chemically similar) crystal bismuth germanium oxide $Bi_{12}GeO_{20}$ (BGO) or bismuth titanium oxide $Bi_{12}TiO_{20}$ (BTO). In other examples, the high bandgap material of the photoconductor layer 74 is a lead-based high bandgap perovskite material such as Methylammonium lead halide ($MAPbX_3$), Formamidinium lead halide ($FAPbX_3$) and Cesium Lead Halide ($CsPbX_3$).

There are several benefits to choosing these photoconductors. All of them contain high-Z materials (for example, Z=83 for Bismuth and Z=82 for lead). This will enhance the x-ray absorption because the photoelectric cross section (absorption power) is proportional to approximately $Z^4$, and photoelectric interactions are dominated in a target x-ray energy range (which are x-rays of a few keV to a few hundred keV) and desirable over other types of interactions like Compton scattering. In addition, these high-Z materials normally have higher densities than low-Z materials like a-Se. However, comparing to the Z difference, this will be of a relative minor effect.

A few other examples of high-bandgap materials for the photoconductor layer 74 are: ZnTe, ZnSe, HgS, TlBr, $HgI_2$ and mercurous halides materials such as $Hg_2I_2$, $Hg_2Br_2$ and $Hg_2Cl_2$. in "H. Chen; J.-S. Kim, F. Jin, and S. Trivedi, "Detection of nuclear radiation via mercurous halides," US Patent Application Pub. No. 2016/0216384.

Figure 3:
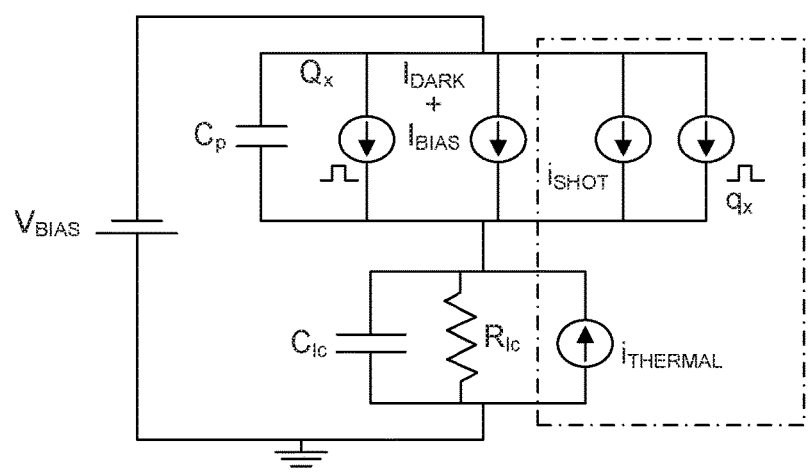
FIG. 3 is a schematic of an equivalent electrical circuit of the photoconductive x-ray detector of FIG. 2.

FIG. 3 shows the effective circuit of the x-ray light valve detector system. As can be seen, the photoconductive assembly 60 can be represented by a capacitor $C_P$ and a number of current and charge sources all connected in parallel. The LC cell 80 can be represented by a capacitor $C_{lc}$ a resistor $R_{lc}$ and a current source all connected in parallel.

With a proper choice of the LC electrical conductivity (not too small and not too large, but larger than that of the photoconductor), at a steady state without x-ray radiation, the voltage drop over the LC cell is low or close to 0 because its thinness and higher electrical conductivity than the photoconductor.

Another important aspect of the choosing LC conductivity is to set the charge relaxation time $\tau_c$ of the device. The drift time of the charges in the photoconductor layer 74 is of the order nanosecond to microsecond depending on the material of the photoconductor layer and the bias voltage ($V_{(bias)}$). This normally is much shorter than the interval between consecutive image frames $\tau_f$ ($1/\tau_f$ being the frame rate). After the charges drift to the LC cell 80, they will dissipate relatively slowly, and this dissipation time is mainly determined by the charge relaxation time of the LC cell 80. LC layer relaxation time is $$\tau_c = \frac{\varepsilon_0 \varepsilon_r}{\sigma} = R_{lc} C_{lc}$$

($\varepsilon_r$ and $\sigma$ are LC dielectric constant and conductivity respectively).

In normal operations, $\tau_f$ should be at least a few times shorter than $\tau_c$ to ensure that the spots created by the charges are captured in multiple frames so that the evolution (blooming) of those spots can be estimated. So, generally, $\tau_f < \tau_c/2$ and preferably $\tau_f < \tau_c/4$. Basically, the LC cell 80 is acting as the charge resetting resistor and capacitor for this purpose.

In general, $\tau_f$ is less than 1 millisecond (msec) for fast imaging and can be longer than seconds for slow imaging. Also, $\tau_c$ is controlled by doping the LC cell 80 to increase its electric conductivity and/or changing its temperature.

Generally, crystalline photoconductors are preferred over amorphous material like a-Se. The advantage of crystalline materials is that they generally have better materials properties (higher electrical mobility, less charge trapping, etc). And the main advantage of amorphous materials is that it can be made of large area in an inexpensive manner. However, for high-resolution detectors described here, the detectors are generally of small area, therefore, this advantage is not very important here to the present system.

In the past for the LC spacer, some have used microrod spacers (as used in LCD display industry), but such spacers are suitable for lower resolution and large area LC light valve applications.

The proposed x-ray detection system is intended for high resolution, small area LC light valve applications. As such, these microrods/microspheres will be visible. Therefore, some embodiments use the edge spacers 86 at the rims of the LC cavity 88. Preferably, the thickness of the spacers 86 and thus the thickness of the LC cavity 88 is 1 μm or less (for high spatial resolution and large dynamic range in dosage).

Polarized reflected light microscopy is a technique that is suitable for examining surfaces containing structures that alter the state of polarization during the reflection and/or light propagation process. For example, structural grains in ore samples and a number of metallic alloys and thin films can be readily examined, along with LC films, using this method. The illuminating wavefronts encounter a polarizer that is placed in the vertical illuminator before the beamsplitter that directs light into the objective. The linearly polarized light waves are focused onto the specimen/mirror surface and reflected back into the objective. After leaving the objective aperture as a parallel bundle of wavefronts, the light is then projected onto a second polarizer (the analyzer) oriented at 90 degrees with respect to the polarizer. Only the depolarized wavefronts are able to pass through the analyzer to reach the tube lens.

Figure 4A:
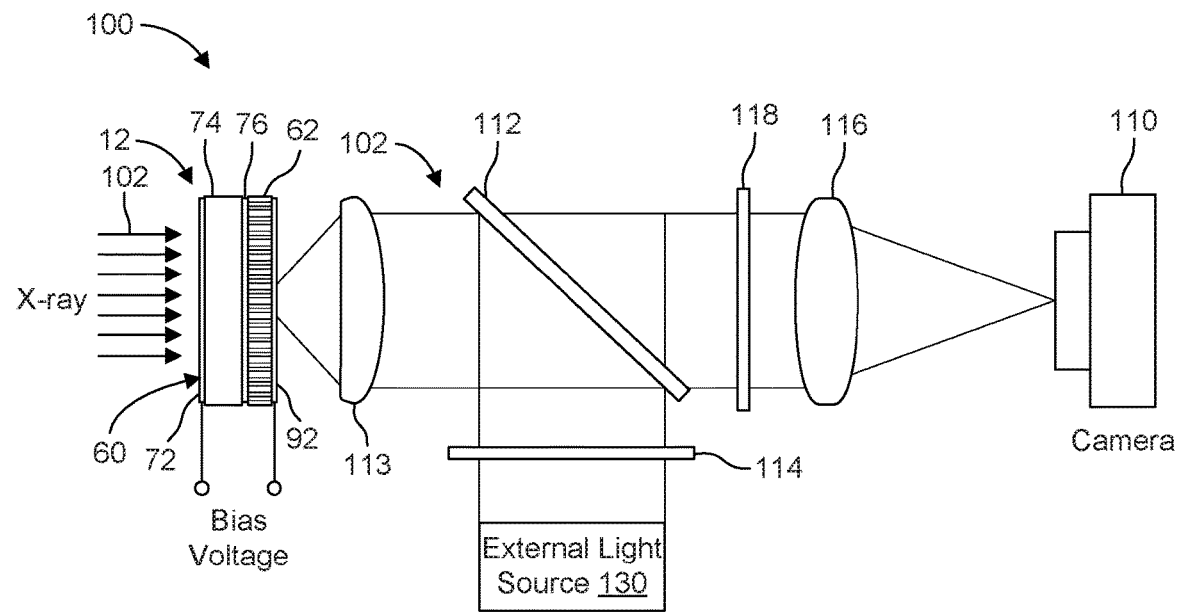
FIGS. 4A and 4B shows two x-ray detection systems employing polarized light optical microscope configurations, operating in reflection and transmission, respectively.
Figure 4B:
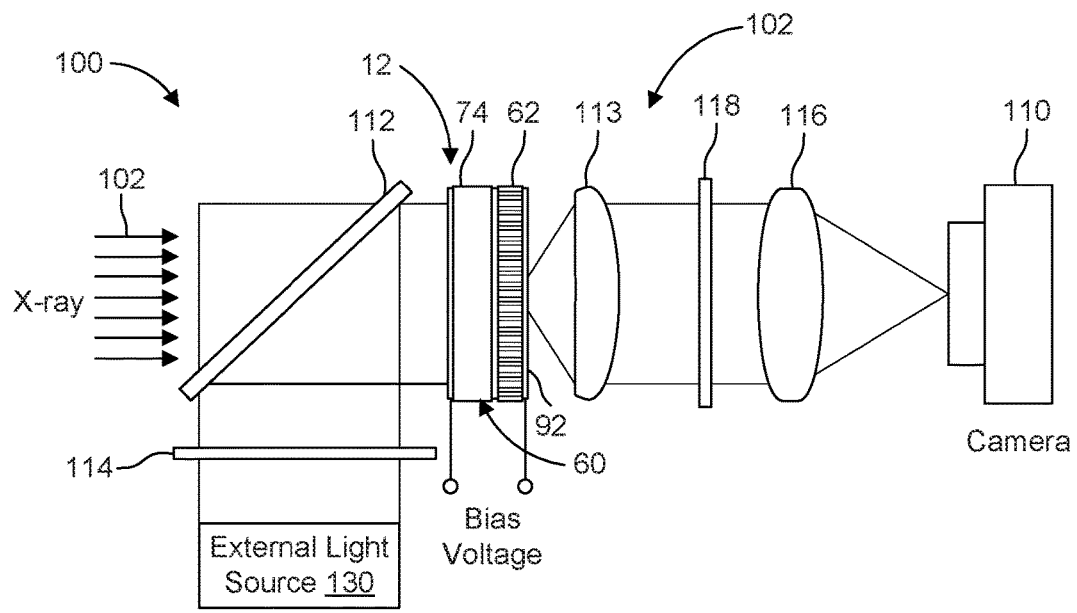

FIGS. 4A and 4B show two possible polarized light optical microscope-based x-ray detection systems 100 that enable the readout of the photoconductive x-ray detector 12 by the camera 110.

In more detail, each of the x-ray detection systems 100 generally comprises the photoconductive x-ray detector 12 and the camera 110, which are coupled to each other via a polarized light optical microscope 102. The photoconductive x-ray detector 12 manifests the x-ray projection of the x-rays 205 in its modulator 62. Then the polarized light optical microscope 102 illuminates the modulator 62 with polarized light for detection by the camera 110.

In FIG. 4A, incoming x-rays or charged particle beam 205 are received in the photoconductor layer 74 of the photoconductive assembly 60. The resulting electric charge forms the image in the modulator 62 of the photoconductive detector 12.

At the same time, the external light source 130 produces light. Examples of the external light source include light emitting diodes (LEDs), laser diodes and filtered incandescent lights. The light is polarized in a polarizer 114, if it is not polarized from the source, and then reflected by a 50/50 beam splitter 112. The light is focused by objective lens 113 onto the spatial light modulator 62. The image recorded in the modulator 62 is manifest in the polarization rotation by the LC cell 80. This light is reflected by reflective layer 76 between the photoconductor layer 74 and the modulator 62. This reflective layer could be a dichroic, thin film mirror. In other cases, the photoconductor layer 74 might be reflective to the wavelength of the light from the external source 130, making the reflective layer 76 unnecessary.

A portion of the reflected light passes through the beamsplitter 112 to a second polarizer 118, which functions as an analyzer. Tube lens 116 forms an image on the camera 110.

In FIG. 4B, the external light source 130 and the beamsplitter 112 are upstream of photoconductive detector 12. The external light is then transmitted through the photoconductive detector 12.

The transmission version shown in FIG. 4B is relatively simple, but prevents the detector 100 from being close to the x-ray or charged particle beam source. In the reflective mode show in FIG. 4A, an extra dielectric mirror 76 is placed onto the photoconductive assembly 60. This dielectric mirror 76 reflects the detecting light back into the optical microscope system to detect the polarization changes in the LC layer. The properties of the dielectric mirror should not interfere the charge transport in the device. For this reason, metallic mirrors are not desired.

In an alternative setup to the transmission mode in FIG. 4B, the analyzer can be placed right after the glass substrate that supports the transparent electrode (or combined with the glass substrate to make a thin analyzer with a transparent electrode). This converts the polarization changes in the LC layer directly to light intensity changes before the light enters the light microscope. The advantage of this alternative is that the expensive and hard-to-get high-NA polarization objective can be replaced by an ordinary high-NA objective.

The lenses in the example diagrams are not limited to microscope objectives.

The system 100 operates as follows to spectrally and spatially resolve the x-ray photons, or other particles. After each x-ray photon (or charged particle) hits the photoconductor layer 74 and is absorbed, it forms many electron-hole pairs. These processes are very fast and can effectively regarded as instantaneous. The next event is the drift of the electrons and hole towards opposite sides of the photoconductor 74, ITO electrode 72 and the interface of the photoconductor 74 and the LC cell 80 of the spatial light modulator 62. We denote the longest of the charge drift time as $\tau_{dr} \approx d^2/\mu V$, where d is the photoconductor thickness, μ is the mobility of the slower charge carrier, and V is the bias voltage. For reasonably good detector materials, $\tau_{dr}$ is at least as small as microsecond scale and can be regarded as instantaneous for most applications. After the charges drift to the LC cell 80, which acts as a lossy capacitor, there are two relevant time scales: the charge relaxation time $\tau_c$, which can vary greatly due to large variation of the liquid crystal conductivity (by doping and temperature); the director relaxation time $\tau_d$, which determines how fast the LC molecules to react to a torque (applied by the change of the electric field) and $\tau_d$ can be a few milliseconds. A simple model only considering the charge and director relaxation time can be written:

$$I(t) = aq\left[1 - \exp\left(-\frac{t}{\tau_d}\right)\right]\exp\left(-\frac{t}{\tau_c}\right),$$

where q is the amount charge drifts to the LC layer; a is the proportional factor that depends on the details of the device configurations; the right two terms with exponential decay form the time factor; l(t) is the total intensity of the signal.

Figure 5:
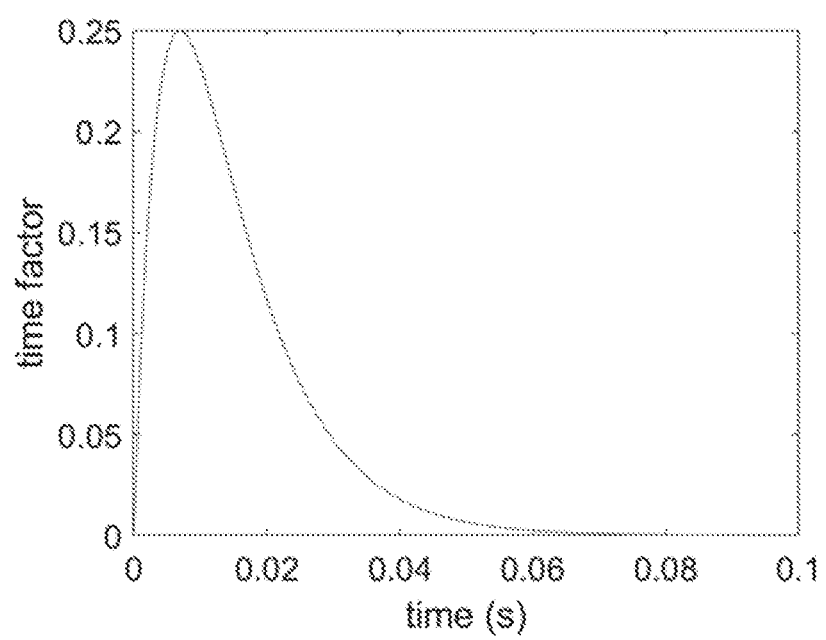
FIG. 5 is a plot of time factor as a function of time in seconds showing the temporal evolution of one spot with $\tau_d$=10 ms and $\tau_c$=10 ms.

FIG. 5 is model signal pulse showing the evolution of the total intensity (only illustrating the time factor) of one photon deposition, with $\tau_d$=10 ms and $\tau_c$=10 ms.

Figure 6:
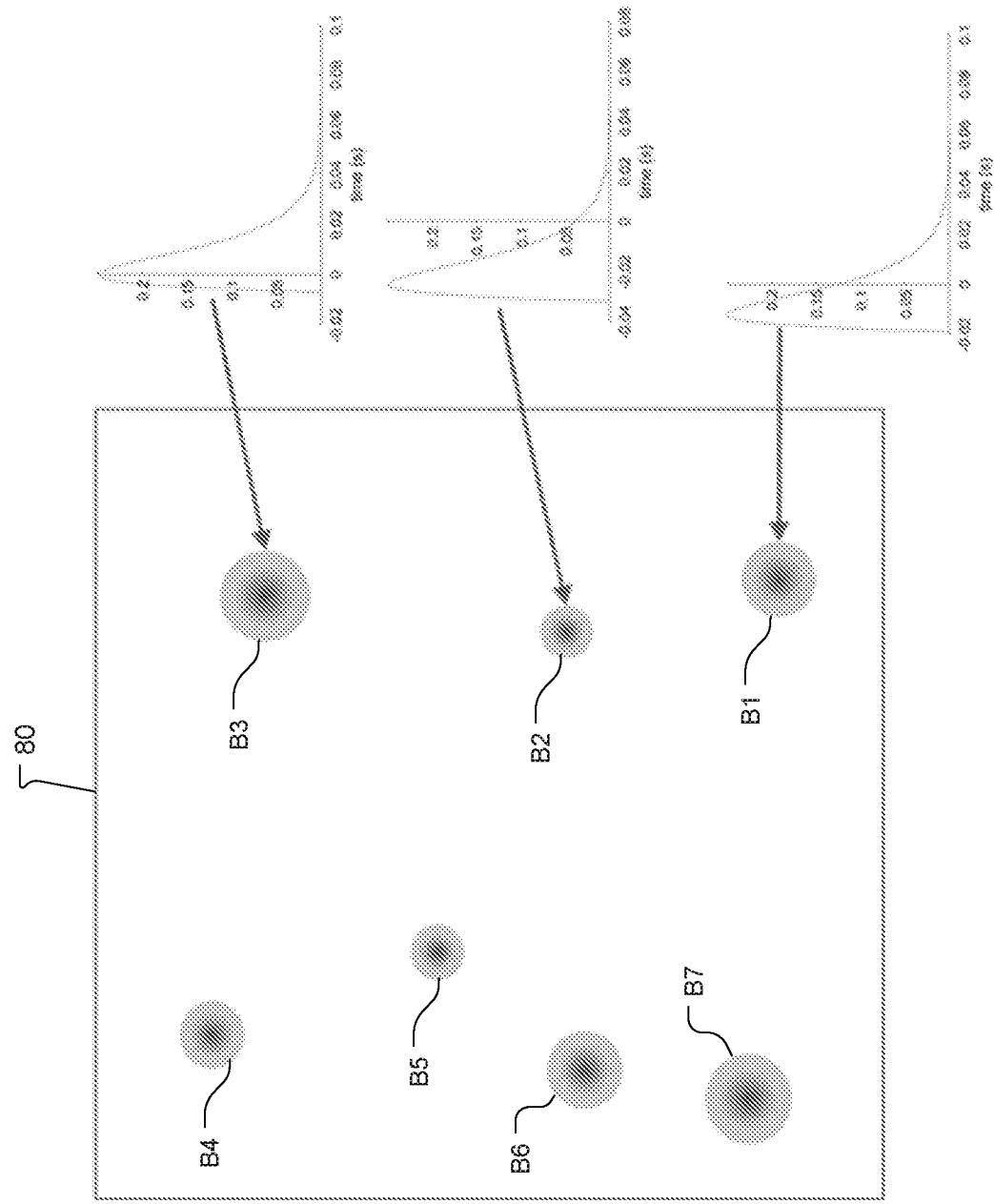
FIG. 6 is a schematic diagram showing spot blooming associated with various detected x-rays or particles across the extent of the photoconductive x-ray detector.

FIG. 6 illustrates one frame of image data captured by the camera 110 at time t=0. A series of spots B1-B7 at different stages of blooming are seen across the extent of the LC cell 80. We have assumed the system is homogeneous and the time constants at different locations are identical. The three blooms at the right sides of the frame are only to illustrate the evolution of the time factor of the individual signal spots. The amount of the charges deposited at each spot can be different and is a function of the energy of the particles that gave rise to the spots.

In any event, by tracking the location of each of the spots and resolving the size of the spot's bloom, and thus the energy of the photon or particle that gave rise to the bloom, a spatially resolved and spectrally (energy) resolved image of the object 214 is generated.

Calibration

Figure 7:
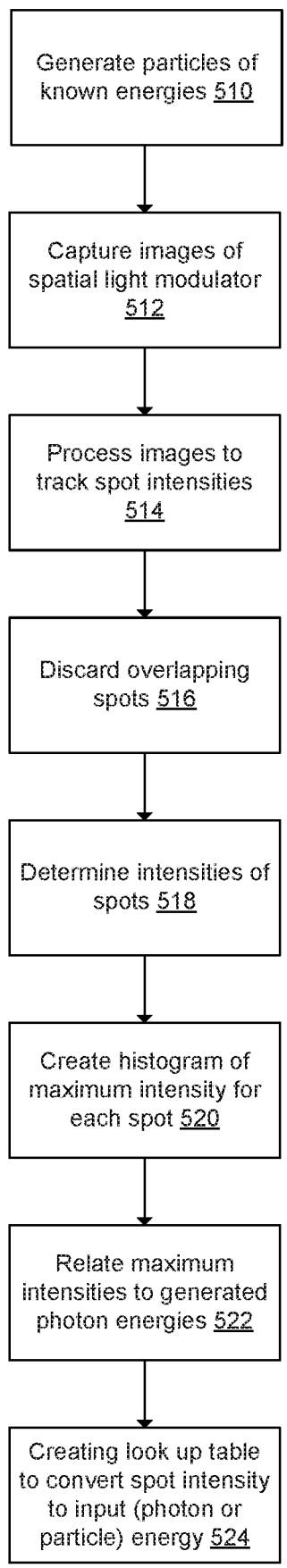
FIG. 7 is a flow diagram showing a method of calibrating the detection system.

FIG. 7 is a flow diagram showing a method for calibrating the imaging spectrometer.

For the calibration, photons or particles of known energies are generated in step 510. A few energy values are needed for the calibration. In one example, the x-ray source system 202 is a set of radioisotopes with the right energy peaks in the detection energy ranges. In another example, the x-ray source system 202 is a tunable synchrotron monogenetic source.

The flux needs to be low, so within relaxation time $$\tau_c = \frac{\varepsilon_0 \varepsilon_r}{\sigma} (\varepsilon_r = \varepsilon_\parallel, \varepsilon_\perp \text{ and } \sigma = \sigma_\parallel, \sigma_\perp$$

depending on the LC alignment) of LC cell 80, individual x-ray deposition events are sparsely distributed as shown in the FIG. 6. Many images of the LC cell are captured by the camera in step 512 and stored.

Next, the images are processed to identify and track the individual spot positions and intensities over the multiple frames within the LC layer relaxation time in step 514. Any overlapping spots are discarded in step 516. The conductivity of the LC layer σ was chosen to set the charge relaxation time to cover a few frames (for higher spectral resolution, use a longer relaxation time; for faster imaging, use a shorter relaxation time).

The relative intensities of the spots are determined in step 518. This can be accomplished by taking the maximum spot intensity, or summing the intensities over the few frames, or curve fitting to the time varying intensities.

Then, in step 520, all the event intensity values of the spots are aggregated to form a histogram plot.

The peaks in the histogram are related to the corresponding input x-ray photon energy in step 522.

The foregoing steps can be repeated with different radioisotopes, for example, producing different input x-ray energies.

Then, an energy/intensity map 310 such as a lookup table (LUT) is produced to convert (with proper interpolation) the spot intensity to the input energy in step 524.

The above calibration can be repeated for a few different bias and imaging conditions. The conditions include the bias amplitudes and frequency and transit rejection conditions.

Figure 8:
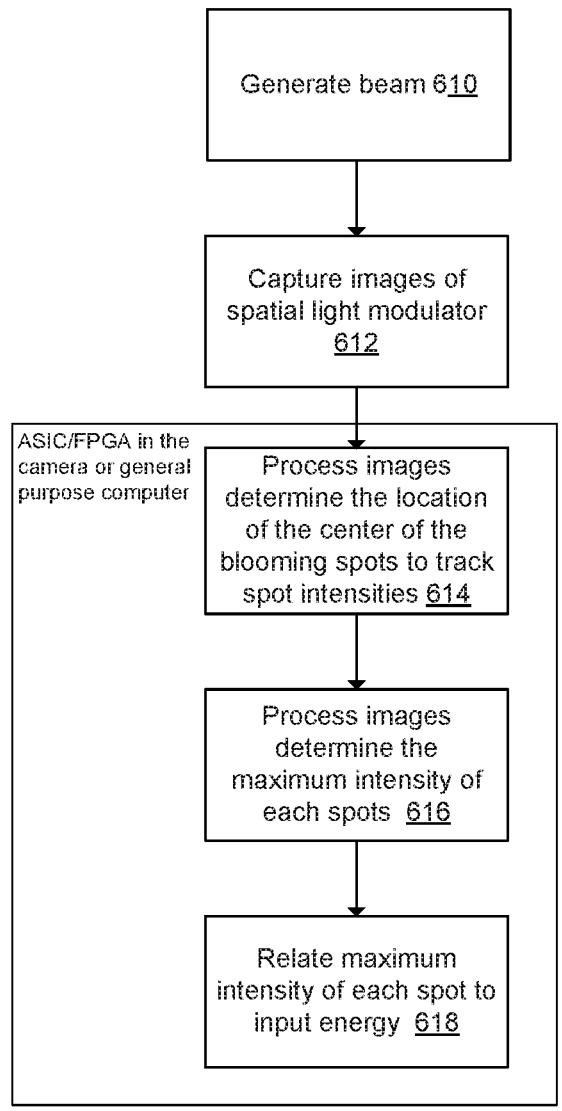
FIG. 8 is a flow diagram showing method of generating an energy resolved image or projection using the detection system.

FIG. 8 describes how the calibrations are used to generate a spectrally and spatially resolved images or projections of the object. 214.

Now, the system 200 is used to carry out the actual spectral imaging except energy of the x-ray (charged particle) source 202 is unknown.

Depending on the spectral accuracy requirements, the device can work with certain level of pileup conditions, i.e. the device can still work when the event spots are overlapping to a small degree. However, the mean spatial photon density/distribution should still be much smaller than the optical resolution of the system. Pileup rejection and correction algorithms can be applied to push the working flux level higher than calibration flux.

In any event, in step 610, the beam 205 is generated to illuminate the object 214.

In step 612, the camera 110 generates images of the spatial light modulator 62 of the photoconductive x-ray detector 12. The images are processed to determine the location, center, of the blooming spots induced by the receipt of the photons or charged particles in step 614.

In step 616, the images are processed to determine the relative intensity of each of the spots over several images using an identical method as in step 518.

Finally, the lookup table (LUT) employed to relate the spot intensity to the input energy in step 618.

Step 614-618 are performed in the computer system, but it need not be a unitary device. For example, the computer system could be a general purpose computer, in which the images have been downloaded and stored, or can be done in a dedicated ASIC/FPGA module as an add-on to the imaging camera or in a GPU. The advantages of such a module are speedup of processing and reduction in data volume and storage.

Analysis

Figure 9:
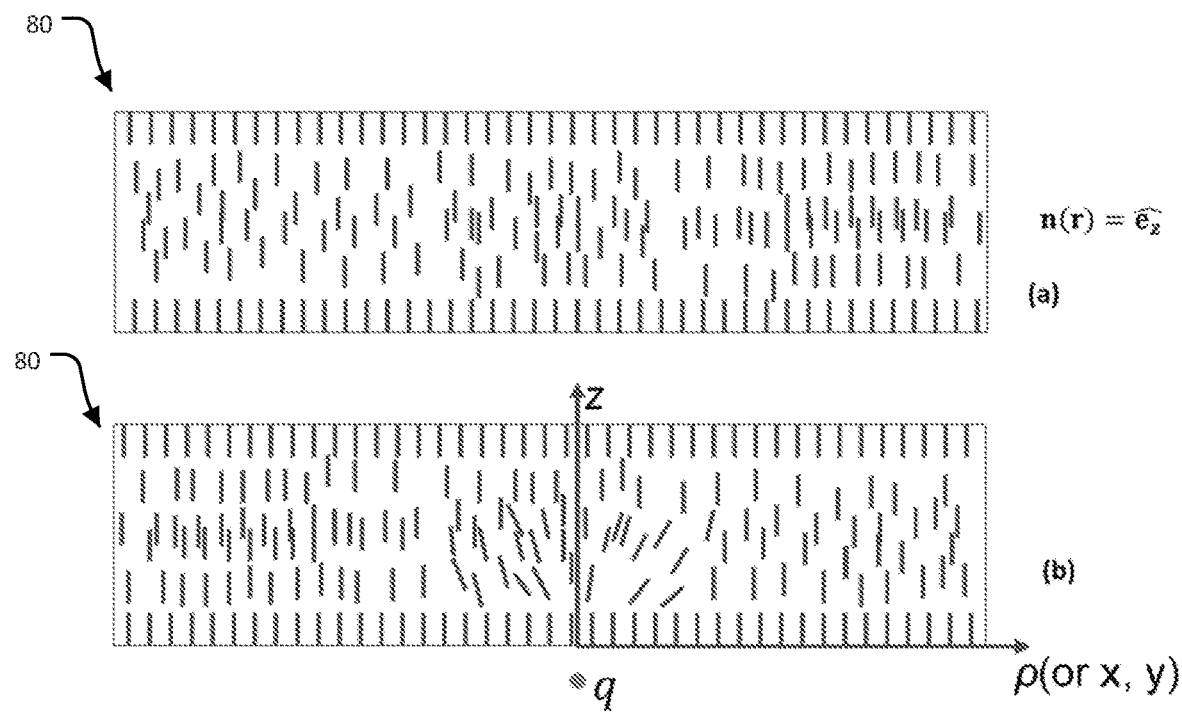
FIG. 9 shows a side cross section of a homeotropic LC cell 80 without an external field showing how the molecules at the two boundaries are anchored strongly and the molecules in the bulk region are forced to follow the same direction, also showing that as a charge q brought close to the LC cell, the directions of the molecules near the charge are bent.

Effect of a Point Charge on a LC Cell:

FIG. 9 illustrates the effect of a point charge near a thin LC cell to show the working principle of the device. Liquid crystal cell 80 is aligned by the two alignment layers 84, 82, above and below. Various alignment directions can be used and we will discuss two possible alignments below. When an x-ray photon is absorbed by the direct-detection material of the photoconductor layer 74, it generates many electron-hole pairs. With external bias electric field, the electrons (or holes if under reversed polarization) drift toward the LC cell. Depending on the conductivity of the LC and alignment layer, the charge will stay near the interface for a finite amount of time. Here we only consider the static case when a charge stays near the interface of a homeotropically aligned LC cell 80 to illustrate the working principle of a LCLV x-ray spectrometer. A charge q is placed near interface by a distance $z_0$. This is an easier case to consider since it has the cylindrical symmetry along z-axis.

It shows the case of the positive dielectric anisotropy where the LC molecules tend to align with external electric field. We assume that the charge is small, director field distortion is small, and therefore the electric field formed by the charge inside the LC cell is approximated by the field without any director distortion. We also assume that the dielectric properties of the two sides of the boundary do not differ too much and therefore we can ignore the effect of the image charge. Because the LC is an anisotropic liquid, this may not be valid, but it can be approximately valid for the case of a small dielectric anisotropy. The following calculations are to illustrate the quantitative pictures, because the large uncertainties of material properties, this only to guide our understanding), we have $$E_\rho = \frac{q\rho}{4\pi\varepsilon_0\varepsilon_\perp r^3}, E_z = \frac{q(z+z_0)}{4\pi\varepsilon_0\varepsilon_\parallel r^3},$$

where $E_\rho$ is the field along radical direction and $E_z$ is the field along z-axis. And $r^2=\rho^2+(z+z_0)^2$, r is the distance from the charge, $\rho$ is the cylindrical radial distance and $z_0$ is the distance from the point charge to the LC interface; $\varepsilon_\parallel$ and $\varepsilon_\perp$ are the parallel and perpendicular dielectrical constants of the LC layer. We will use a one-constant approximation to try to solve the director field by this charge. For $n_x$ and $n_y$, we have $$K\nabla^2 n = -\varepsilon_0\varepsilon_a(n\cdot E)E,$$

where K is the average of the three elastic constants and $\varepsilon_a = \varepsilon_\parallel - \varepsilon_\perp$. Written in cylindrical coordinates, we have $$K\left(\nabla^2 n_\rho - \frac{n_\rho}{\rho^2}\right) = -\varepsilon_0\varepsilon_a\left(n_\rho E_\rho + \sqrt{1-n_\rho^2}E_z\right)E_\rho \approx -\varepsilon_0\varepsilon_a E_z E_\rho$$

Figure 10A:
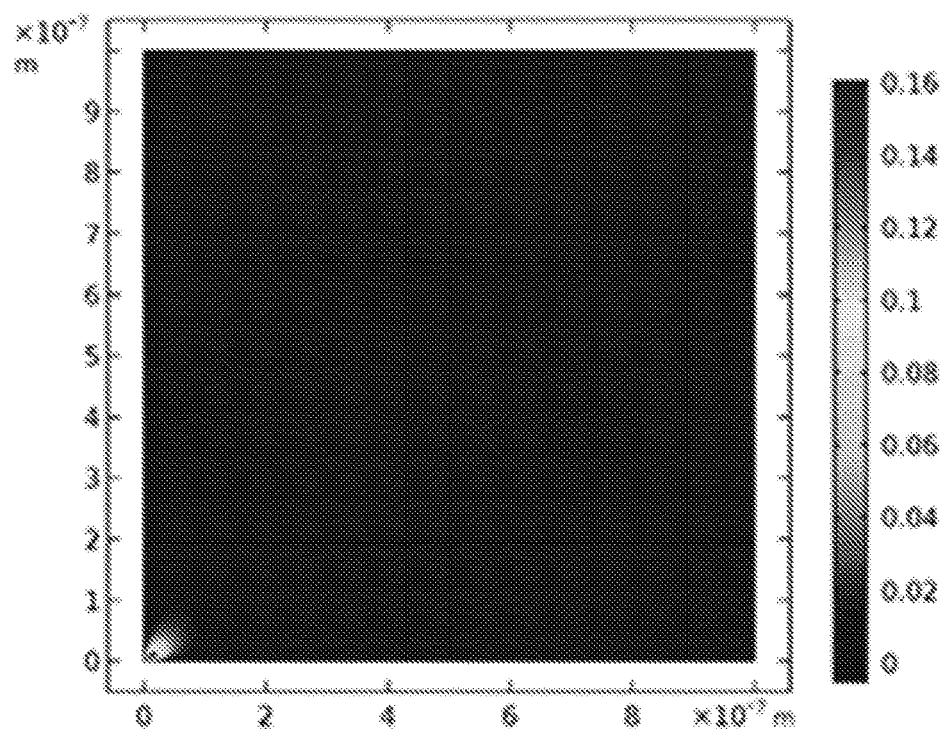
FIGS. 10A and 10B show a simulation result for a 1 μm thick LC homeotropic cell. The parameters used in the simulation are: K=10 pN, $\varepsilon_\parallel$=15, $\varepsilon_\perp$=3, $z_0$=10 nm, q=60e.
Figure 10B:
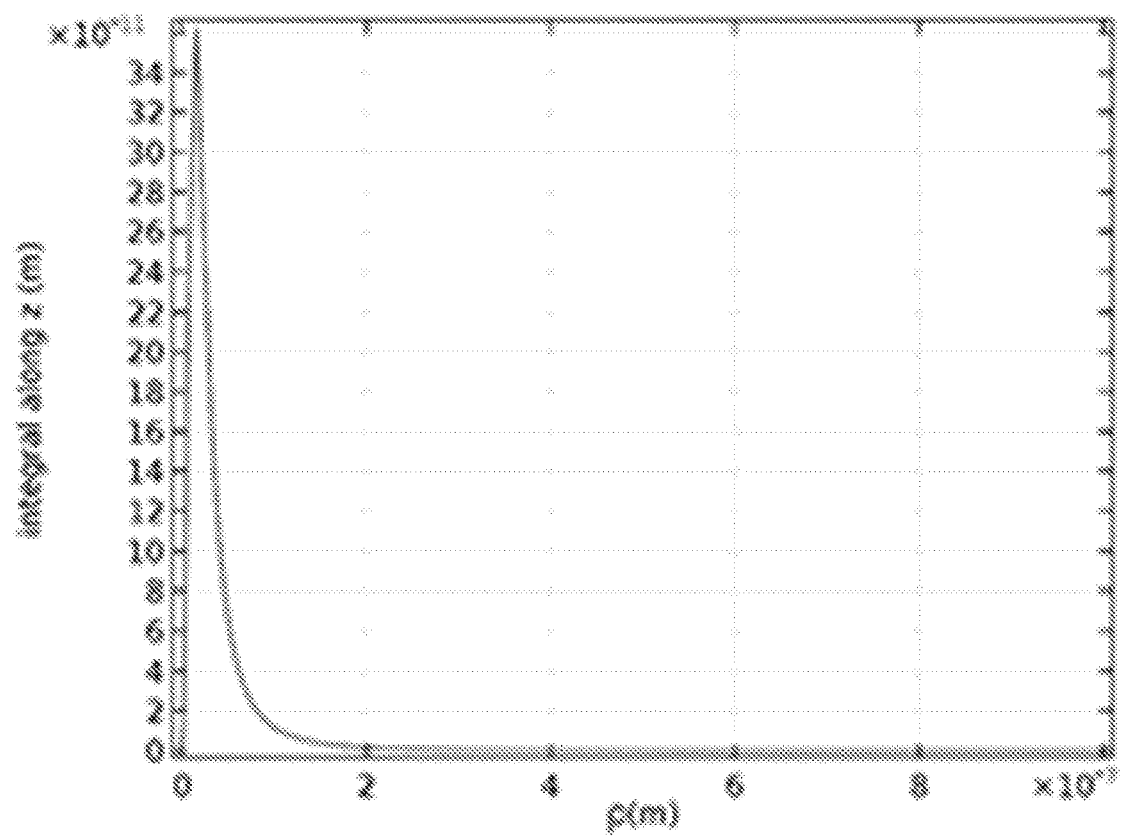

FIG. 10A shows the simulated result for one typical case of the homeotropic alignment with LC layer thickness d=1 μm (The parameter used in the simulation were: K=10 pN, $\varepsilon_\parallel$=15, $\varepsilon_\perp$=3, $z_0$=10 nm, q=60e). For small tilts, $n_\rho$ is identical with the director angle (in unit of radian) with respect to z-axis θ. It can be shown that for optical detection, if not considering the diffraction effect, the optical signal is proportional to $\int \theta^2 dz$, where the integration is over the z-axis along the detection light propagation. FIG. 10B shows the integrated result.

We can see the effect of the point charge is very narrow and it is concentrated near the charge position. This is partially due to the fact that in the director equation, the force term is proportional to the electric field squared. This nonlinear dependence will make the output of the signal nonlinearly dependent on the charge deposition, which is not desirable. However, with the addition of flexoelectric effect, which has a term linearly dependent on the electric field, the situation will be modified and we will discuss the issue below. In addition, the shape of the LC director tilt is like a donut. This is because at the point right above the charge, the electric field points upward and tilt is zero. The size of the donut is of order tenths of micron and if observed with visible light, we will not be able to see the central dark region.

For a planar alignment, we can solve the director partial differential equation (PDE) similarly. However, it is a 3D PDE and therefore more complicated. For a perfect planar aligned cell with similar geometry, we have the electric field (director align along x-axis when there is no charge).

$$E_x = \frac{qx}{4\pi\varepsilon_0\varepsilon_\parallel r^3}, E_y = \frac{qy}{4\pi\varepsilon_0\varepsilon_\perp r^3}, E_z = \frac{q(z+z_0)}{4\pi\varepsilon_0\varepsilon_\perp r^3}.$$

Figure 11A:
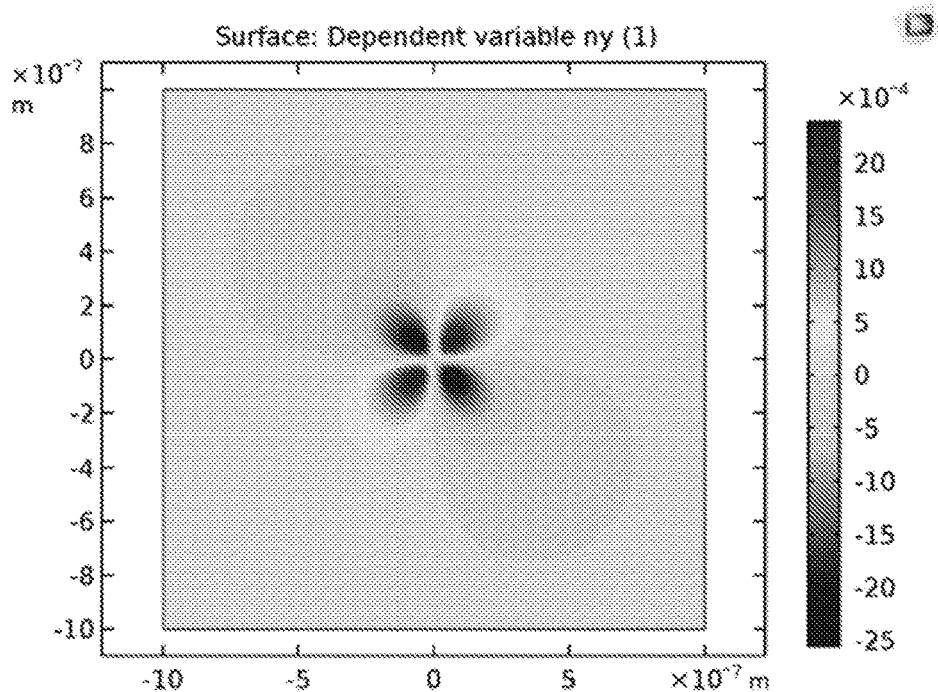
FIGS. 11A and 11B show a simulation result for a 1 μm thick LC planar cell. The parameter used in the simulation are: K=10 pN, $\varepsilon_\parallel$=15, $\varepsilon_\perp$=3, $z_0$=10 nm, q=62e. (a) $n_y$; (b) $n_z$.
Figure 11B:
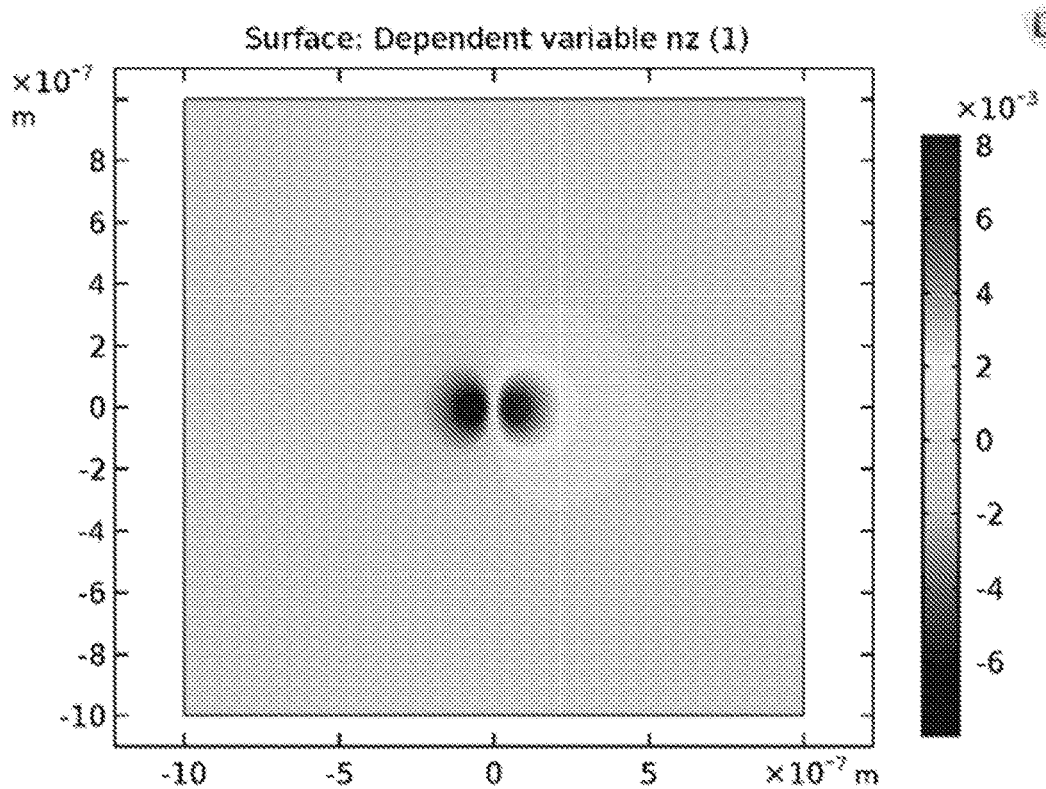

FIGS. 11A and 11B show the simulated result for one typical case of the planar alignment with LC layer thickness d=1 μm (The parameter used in the simulation were: K=10 pN, $\varepsilon_\parallel$=15, $\varepsilon_\perp$=3, $z_0$=10 nm, q=62e). Note that negative and positive values of n are equivalent. The effects of the director distortions under observing light are rather complicated and in these simulations, we have not considered the flexoelectric effect and it can be strong at small scales, therefore, this simulation result is only to illustrate the result for planar alignment.

For the liquid crystal director distortion problems we are considering here, because the electric field is highly concentrated and nonuniform, the flexoelectric effect can be strong at small scale. Below we illustrate the effect for homeotropic case. Because there are a lot of uncertainties in the measured flexoelectric coefficients $e_1$ and $e_3$ of all the published results, our results here are only to illustrate the possible results. The actual results need to be measured and calibrated for individual LC cells.

Including the flexoelectric effect, the director equation becomes:

$$K\nabla^2 n = -\varepsilon_0\varepsilon_a(n\cdot E)E - (e_1-e_3)[E(\nabla\cdot n)-(\nabla n)\cdot E]+(e_1+e_3)n\cdot\nabla E.$$

To simplify the problem, we only consider the homeotropic case. Because of the cylindrical symmetry, we can rewrite it in cylindrical coordinates:

$$K\left(\nabla^2 n_\rho - \frac{n_\rho}{\rho^2}\right) =$$

$$-\varepsilon_0\varepsilon_a\left[n_\rho E_\rho + E_z\sqrt{1-n_\rho^2}\right]E_\rho - (e_1-e_3)\left[E_\rho\left(\frac{1}{\rho}\frac{\partial(\rho n_\rho)}{\partial\rho} + \frac{\partial\sqrt{1-n_\rho^2}}{\partial z}\right) - E_\rho\frac{\partial n_\rho}{\partial\rho} - E_z\frac{\partial n_\rho}{\partial z}\right] +$$

$$(e_1+e_3)\left(n_\rho\frac{\partial E_\rho}{\partial\rho} + \sqrt{1-n_\rho^2}\frac{\partial E_\rho}{\partial z}\right) = -\varepsilon_0\varepsilon_a\left[n_\rho E_\rho + E_z\sqrt{1-n_\rho^2}\right]E_\rho -$$

-continued $$(e_1 - e_3)\left[E_\rho\left(\frac{n_\rho}{\rho} - \frac{n_\rho}{\sqrt{1-n_\rho^2}}\frac{\partial n_\rho}{\partial z}\right) - E_z\frac{\partial n_\rho}{\partial z}\right] + (e_1 + e_3)\left(n_\rho\frac{\partial E_\rho}{\partial \rho} + \sqrt{1-n_\rho^2}\frac{\partial E_\rho}{\partial z}\right) \approx$$

$$-\varepsilon_0\varepsilon_a E_z E_\rho - (e_1 - e_3)\left[E_\rho\left(\frac{n_\rho}{\rho} - n_\rho\frac{\partial n_\rho}{\partial z}\right) - E_z\frac{\partial n_\rho}{\partial z}\right] + (e_1 + e_3)\frac{\partial E_\rho}{\partial z}.$$

And $$E_\rho = \frac{q\rho}{4\pi\varepsilon_0\varepsilon_\perp r^3}, E_z = \frac{q(z+z_0)}{4\pi\varepsilon_0\varepsilon_\parallel r^3}; \frac{\partial E_\rho}{\partial \rho} = \frac{q}{4\pi\varepsilon_0\varepsilon_\perp}\left(\frac{1}{r^3} - \frac{3\rho^2}{r^5}\right), \frac{\partial E_\rho}{\partial z} = \frac{-3q\rho}{4\pi\varepsilon_0\varepsilon_\perp}\frac{(z+z_0)}{r^5}$$

Figure 12A:
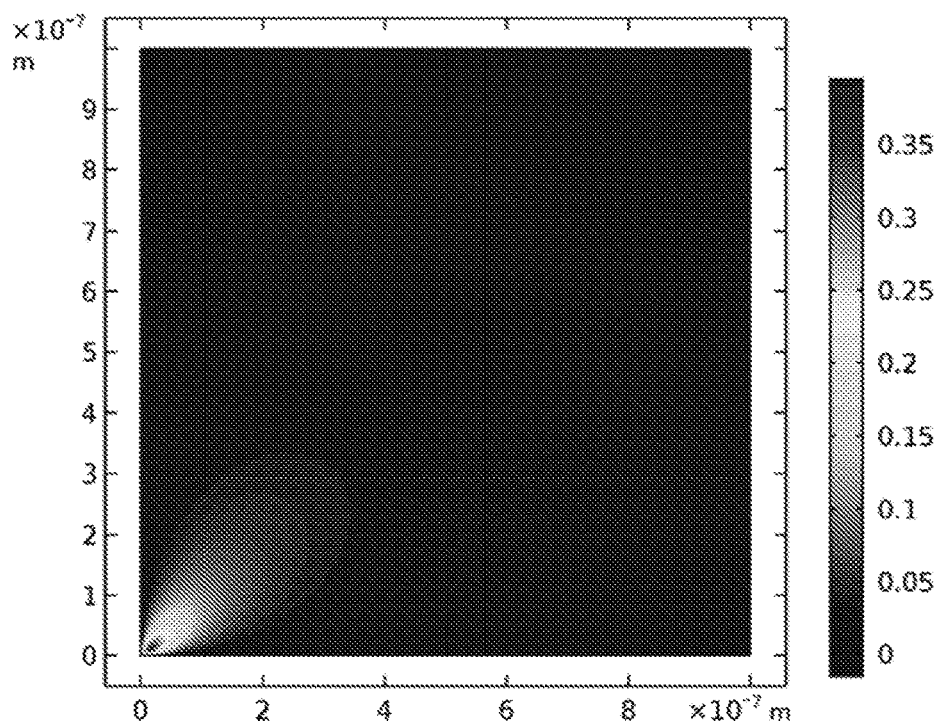
FIGS. 12A and 12B show simulation results for a 1 μm thick LC homeotropic cell with flexoelectric effect. The parameter used in the simulation are: K=10 pN, $e_1-e_3$=12.2 pC/m, $e_1+e_3$=40.0 pC/m, $\varepsilon_\parallel$=15, $\varepsilon_\perp$=3, $z_0$=10 nm, q=33e.
Figure 12B:
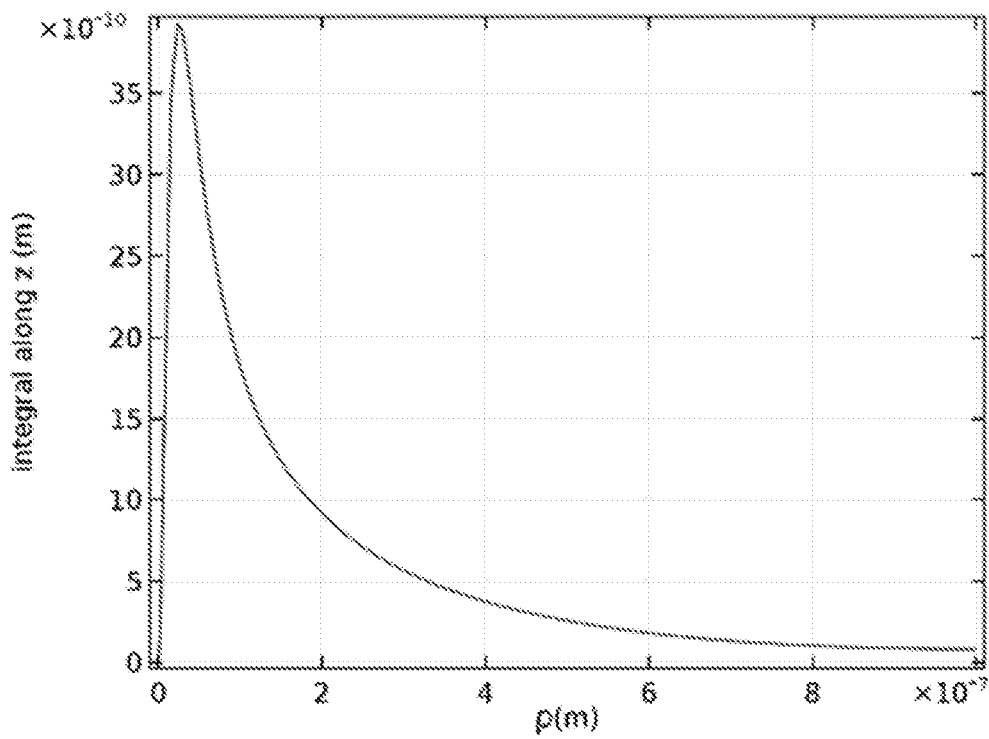

FIGS. 12A and 12B show the simulation results for a 1 μm thick LC homeotropic cell with flexoelectric effect (The parameter used in the simulation were: K=10 pN, $\varepsilon_\parallel$=15, $\varepsilon_\perp$=3, $z_0$=10 nm, q=33e, $e_1-e_3$=12.2 pC/m, $e_1+e_3$=40.0 pC/m). Because the linear dependence of electric field in the flexoelectric terms, they are dominant over the squared electric term at low charge case, which is of primary interest to us. Therefore, it modifies the results greatly. However, because there are a lot of uncertainties in the values of $e_1$ and $e_3$, our calculations only illustrate the effect. With our chosen values ($e_1-e_3$=12.2 pC/m, $e_1+e_3$=40.0 pC/m), flexoelectric effect makes the LC detector more sensitive to small charge deposition. In addition, the effect makes it more linear at small charge deposition. However, the range of the director tilt becomes larger.

In the above discussion, we have assumed that the external applied field along z-axis is 0 and this is achieved when the external bias voltage over the light valve (photoconductor in series with the LC layer) is low and the LC layer has relatively high conductivity (for example, by doping the LC with ionic salt). In the other cases, when the external bias voltage is high and the LC is not highly conductive, there usually a voltage drop over the LC layer and the bias field caused by the external field along z-axis is mostly much larger than the field caused by the point charge. In this case, the director equation becomes $$K\left(\nabla^2 n_\rho - \frac{n_\rho}{\rho^2}\right) \approx -\varepsilon_0\varepsilon_a(E_{z0} + E_z)E_\rho.$$

And when $E_{z0} \gg E_z$ at most locations, we have $$K\left(\nabla^2 n_\rho - \frac{n_\rho}{\rho^2}\right) \approx -\varepsilon_0\varepsilon_a E_{z0} E_\rho.$$

Again, the force term is now linearly dependent on the E-field caused by the point charge.

Figure 13A:
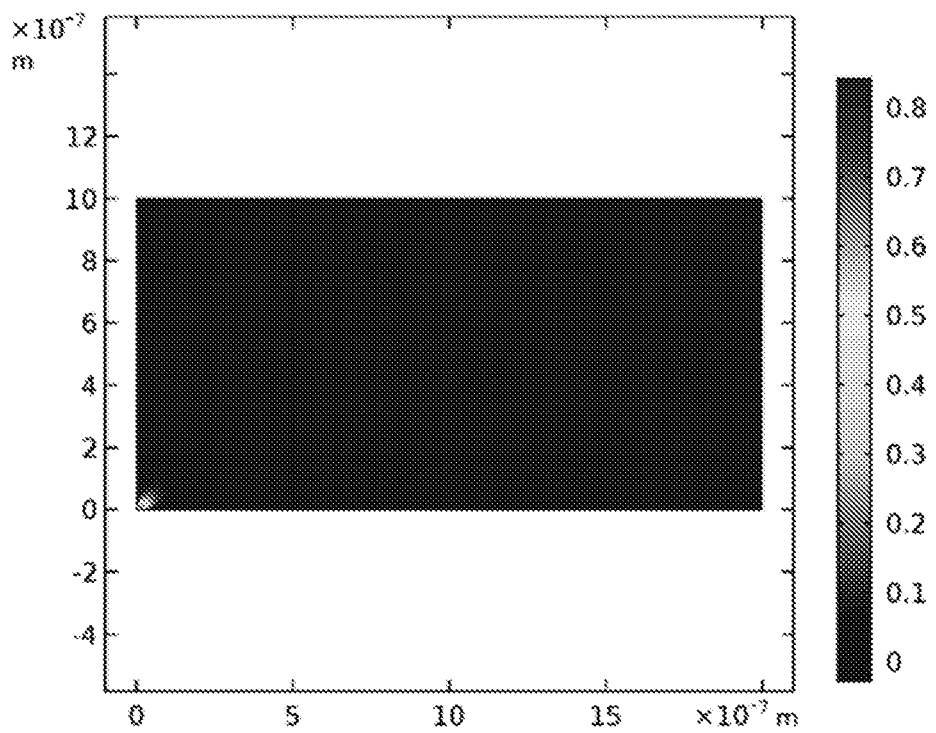
FIGS. 13A and 13B show simulation results for a 1 μm thick LC homeotropic cell including a bias z-direction field. The parameter used in the simulation are: K=10 pN, $\varepsilon_\parallel$=15, $\varepsilon_\perp$=3, $z_0$=10 nm, q=95e, $E_{z0}$32 0.5 V/m.
Figure 13B:
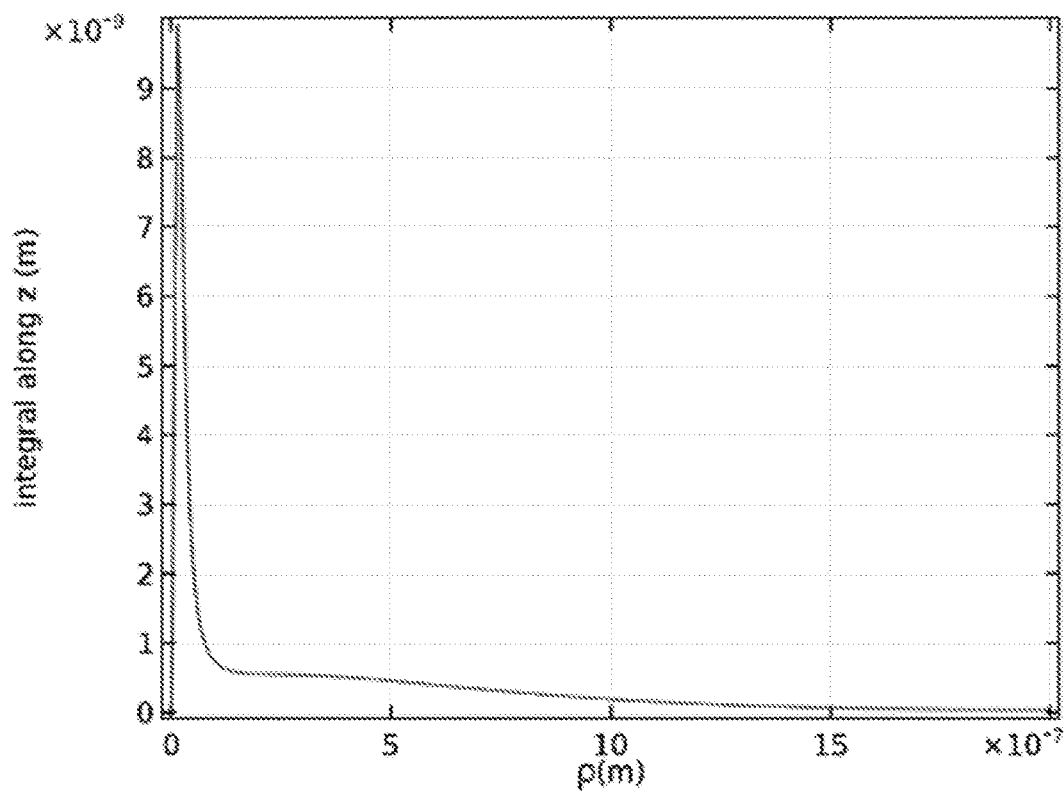

FIGS. 13A and 13B show the simulation results for a 1 μm thick LC homeotropic cell with a bias field $E_{z0}$=0.5 V/μm (The parameter used in the simulation were: K=10 pN, $\varepsilon_\parallel$=15, $\varepsilon_\perp$=3, $z_0$=10 nm, q=95e). It becomes more sensitive comparing without the bias field. However, the range of the area affected by the charge increased to cover a much bigger area. Since the bias field can be tuned, this can be one of the adjustable parameter to control the LCLV. If both the flexoelectric and the bias field are included in the calculation, the effects are combined (in flexoelectric effect and large bias field cases, the equation becomes linearly dependent on the charge induced field, the effects can be linearly combined when these two effects are strong.)

Figure 14A:
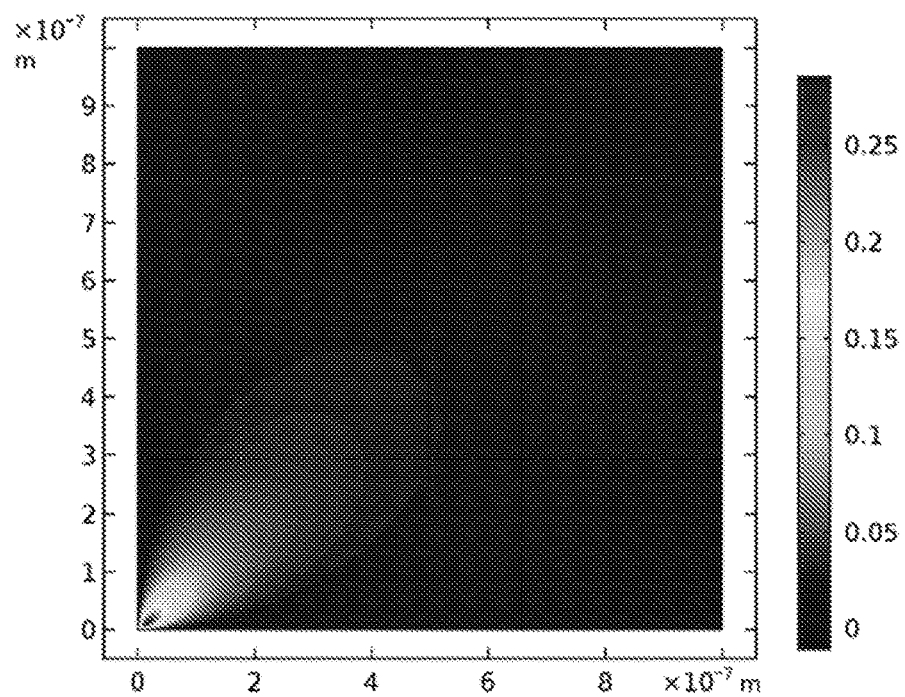
FIGS. 14A and 14B show simulation results for a 1 μm thick LC homeotropic cell with flexoelectric effect and a bias z-directional field. The parameter used in the simulation are: K=10 pN, $e_1-e_3$=12.2 pC/m, $e_1+e_3$=40.0 pC/m, $\varepsilon_\parallel$=15, $\varepsilon_\perp$=3, $z_0$=10 nm, q=25e, $E_{z0}$=0.5 V/m.
Figure 14B:
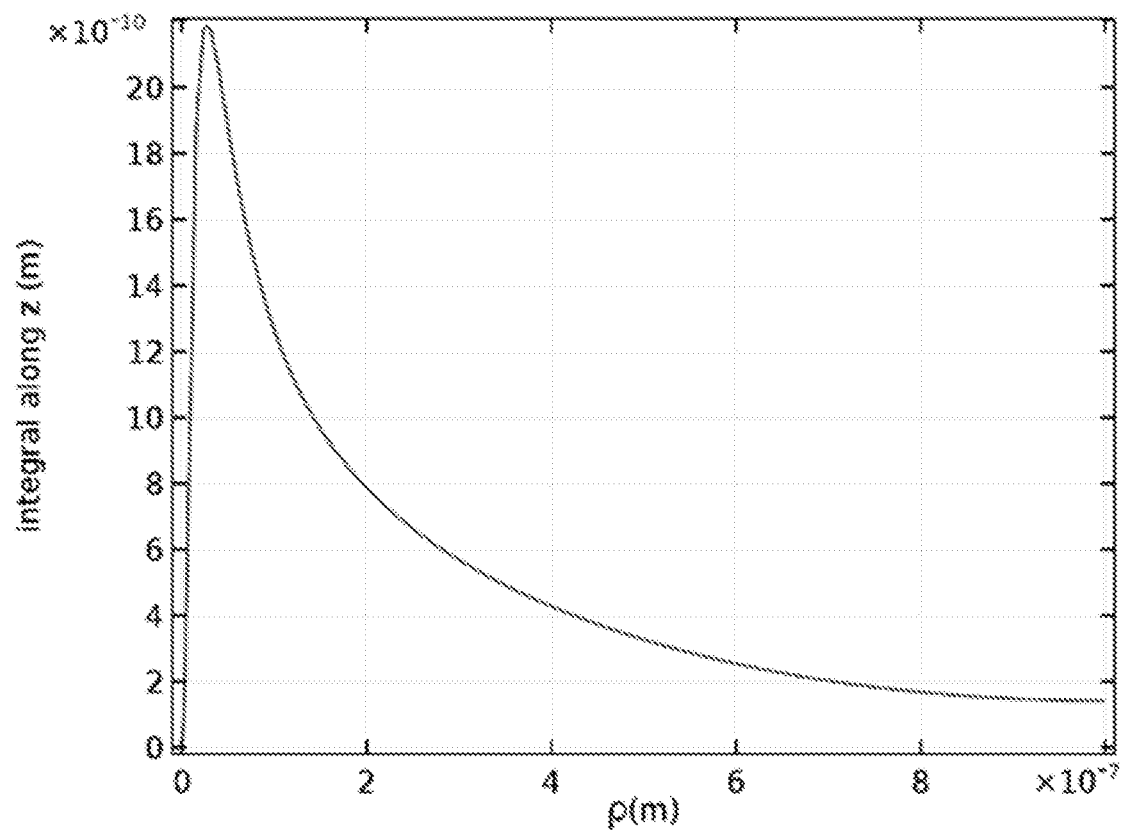

FIGS. 14A and 14B show the calculated results with both effects included (The parameter used in the simulation were: K=10 pN, $\varepsilon_\parallel$=15, $\varepsilon_\perp$=3, $z_0$=10 nm, q=25e, $e_1-e_3$=12.2 pC/m, $e_1+e_3$=40.0 pC/m, $E_{z0}$=0.5 V/m). This is rather similar to the case with flexoelectric effect only. However, with different material parameters, different combinations can happen.

LC Cell Sensitivity

There are multiple factors affecting the sensitivity of using a LC cell to detect a point charge, such as the detecting light intensity and various alignment factors. In theory, the ultimate factor is the thermal noise induced tilt of the director field.

It can be shown (P. G. de Gennes and J. Prost, *The Physics of Liquid Crystals*. Clarendon Press, 1995) that for bulk liquid crystal (LC) whose director is aligned along z-direction, $$\langle |n_\alpha(q)|^2\rangle = \frac{\Omega k_B T}{K_3 q_\parallel^2 + K_\alpha q_\perp^2 + \epsilon_0\epsilon_a E^2}.$$

For our simplified case, $K_3=K_\alpha=K$. $n_1=\sin\theta\cos\varphi$ and $n_2=\sin\theta\sin\varphi$, therefore $\theta^2 \approx \sin^2\theta = n_1^2 + n_2^2$, we have $$\langle |\theta(q)|^2\rangle \approx \langle |n_\alpha(q)|^2\rangle = \frac{\Omega k_B T}{Kq^2 + \epsilon_0\epsilon_a E^2} = \frac{\Omega k_B T}{K(q_z^2 = q_\rho^2) + \epsilon_0\epsilon_a E^2}.$$

For our cases, q's in z-direction are discretized due to the confined by the two boundaries, $$q_z = \frac{m\pi}{d},$$

where m is an integer. $q_\rho$ is the wavenumber in x-y plane and $\rho^2=x^2+y^2$. And for each $q_z$ mode, the z-dependence of $\theta_m \propto$ $$\sin\left(\frac{m\pi z}{d}\right),$$

where m is an integer and this satisfies the boundary conditions $\theta_m(0)=\theta_m(d)=0$.

To get the θ fluctuations for each $q_z$ mode, we integrate over $q_\rho$ from $$q_1 = \frac{2\pi}{L} \text{ to } q_2 = \frac{2\pi}{\rho_b},$$

where L is the lateral size of the liquid crystal layer and $\rho_b$ is the feature size in x-y direction (have been set to 0.5 μm in all the examples).

$$\langle \theta_m^2 \rangle = \left(\frac{2}{d}\right)^2 \left(\frac{1}{4\pi^2} \frac{1}{\pi L^2}\right) \frac{\Omega k_B T}{K} \int_{q_1}^{q_2} dq_\rho \frac{2\pi q_\rho}{\left(q_z^2 + q_\rho^2 + \frac{\epsilon_0 \epsilon_a}{K} E^2\right)} =$$

$$\frac{k_B T}{\pi d K} \ln\left(\frac{q_z^2 + \frac{\epsilon_0 \epsilon_a}{K} E^2 + q_2^2}{q_z^2 + \frac{\epsilon_0 \epsilon_a}{K} E^2 + q_1^2}\right).$$

We have $$\Omega = \pi L^2 d; \left(\frac{2}{d}\right)^2$$

factor is to make the result dimensionless; factor $$\left(\frac{1}{4\pi^2} \frac{1}{\pi L^2}\right)$$

accounts for 2-dimensional integration over wavenumber $dq_\rho dq_\rho$ ($\pi L^2$ is the area, $$\frac{1}{4\pi^2}$$

accounts for converting sum over $q_x$, $q_y$ to integration). In the case the lateral size of LC layer is much larger than the thickness of the LC layer, we have $$\langle \theta_m^2 \rangle = \frac{k_B T}{\pi d K} \ln\left(1 + \frac{q_2^2}{q_z^2 + \frac{\epsilon_0 \epsilon_a}{K} E^2}\right).$$

This expression shows that the lowest mode m=1 induced the largest director tilt and we can treat this as a typical fluctuation amplitude. Plugging in the values used in the above examples K=10 pN, $\epsilon_a$=12, d=1 µm, for feature size $\rho_b$=0.5 µm, we have $\sqrt{\langle \theta_1^2 \rangle}$=0.0185 rad if $E_{z0}$=0.5V/µm and $\sqrt{\langle \theta_1^2 \rangle}$=0.0193 rad if no external bias field.

To get the sensitivity of the device to one point charge, we compare the integrated induced director tilt $\int_0^d \theta^2 dz$ average over a cylinder of radius $\rho_b$ with the thermal induced mean tilt $$\sum_{m=1}^\infty \langle \theta_m^2 \rangle \int_0^d \sin^2\left(\frac{m\pi z}{d}\right) dz = \frac{d}{2} \sum_{m=1}^\infty \langle \theta_m^2 \rangle$$

For the values used in the above examples K=10 pN, $\epsilon_a$=12, d=1 µm, for feature size $\rho_b$=0.5 µm, we have $\sum_{m=1}^\infty \langle \theta_m^2 \rangle$=1.18×10$^{-3}$ rad$^2$ if $E_{z0}$=0.5V/µm and $\sum_{m=1}^\infty \langle \theta_m^2 \rangle$=1.22×10$^{-3}$ rad$^2$ if no external bias field.

| Effects | No bias field, no flexoelectric effect | No bias field, with flexoelectric effect | bias field 0.5 V/µm, no flexoelectric effect | bias field 0.5 V/µm, with flexoelectric effect |
|---|---|---|---|---|
| Sensitivity (e) | N/A | 33 | 95 | 25 |

This table shows the sensitivity of a 1 µm LC cell including the different effects considered (K=10 pN, $e_1-e_3$=12.2 pC/m, $e_1+e_3$=40 pC/m, $\epsilon_\parallel$=15, $\epsilon_\perp$=3, $z_0$=10 nm, $E_{z0}$=when a bias is applied). In the case of no bias field and no flexoelectric effect, the direct tilt is highly localized and the calculation will yield a tilt that violates the approximation $|n| \ll 1$, therefore no result was listed. We can see that the homeotropic LC cell is rather sensitive to the charges (the case of 25e roughly corresponds about 75 to 200 eV detector energy resolution).

Spectral Resolution

There are a few factors to increase the spectral width (lower energy resolution):

Fundamental thermal noise induced director tilt as described above.

Finite number of the detecting photons. Although we can provide rather high intensity illumination, when the camera exposure time is short, this could be an important source of noise.

Camera noise.

Depending on the depth of the deposition, part of electrons or holes are absorbed by the photoconductor and if this absorption is too much, we will get a very big spread of the peak width. Therefore, one of most important criteria for choosing the right photoconductor is the mu-tau product (mobility and lifetime product) of the photoconductor, which along with the bias voltage and thickness of the photoconductor, determines the absorption of the charge carrier. Fortunately, for most of our detection tasks, our resolution requirement dictates that the photoconductor has to be rather thin. Therefore, with moderate mu-tau product and bias voltage, we should be able to get a rather high collection efficiency.

While this invention has been particularly shown and described with references to preferred embodiments thereof, it will be understood by those skilled in the art that various changes in form and details may be made therein without departing from the scope of the invention encompassed by the appended claims.

What is claimed is:

1. A spectrally and spatially resolved x-ray and/or charged particle detection system, comprising:
    a photoconductive detector;
    an optical microscope for reading out the photoconductive detector;
    a camera coupled to the photoconductive detector by the optical microscope; and
    a computer system that obtains images generated by the camera and tracks the response of the photoconductive detector to x-ray photons and/or charged particles over time.

2. The detection system as claimed in claim 1, wherein the computer system tracks blooming in the photoconductive detector induced by the x-ray photons or charged particles to resolve locations on the photoconductive detector and energy of the x-ray photons or charged particles.

3. The detection system as claimed in claim 1, wherein the computer system determines the energy of the x-ray photons or charged particles by reference to an energy/intensity map that relates a maximum spot intensity to an energy of the received x-ray photons or charged particle.

4. The detection system as claimed in claim 1, wherein an interval between successive frames captured by the camera is less than a relaxation time of the photoconductive detector.

5. The detection system as claimed in claim 4, wherein an interval between successive frames captured by the camera is less than 1 millisecond.

6. The detection system as claimed in claim 1, wherein the photoconductive detector detects x-ray photons.

7. The detection system as claimed in claim 1, wherein the photoconductive x-ray/charged particle detector comprises a liquid crystal light valve and photoconductive detector layer.

8. The detection system as claimed in claim 7, wherein the photoconductive detector layer comprises bismuth, lead, mercury, tellurium, selenium, or thallium.

9. The detection system as claimed in claim 1, wherein the optical microscope is a polarization light microscope.

10. The detection system as claimed in claim 1, wherein the optical microscope reads-out the photoconductive detector in transmission.

11. The detection system as claimed in claim 1, wherein the optical microscope reads-out the photoconductive detector in reflection.

12. A particle detection method, comprising:
converting x-ray photons and/or charged particles into electron-hole pairs in a photoconductive detector;
reading out the photoconductive detector with a camera coupled to the photoconductive detector; and
processing images generated by the camera and tracking the response of the photoconductive detector to x-ray photons or charged particles over time to determine the position and the energy of the x-ray photons or charged particles.

13. The method of claim 12 employing a system comprising:
the photoconductive detector;
an optical microscope for reading out the photoconductive detector;
the camera coupled to the photoconductive detector by the optical microscope; and
a computer system that obtains images generated by the camera and tracks the response of the photoconductive detector to x-ray photons and/or charged particles over time.

14. An imaging system, comprising:
an object stage system for holding an object;
a photoconductive detector for detecting x-ray photons or charged particles from the object;
a camera coupled to the photoconductive detector by an optical microscope; and
a computer system that obtains the images generated by the camera and tracks the response of the photoconductive detector to x-ray photons or charged particles over time to image the object and determine an energy of the x-ray photons or charged particles.

15. A method for calibrating a x-ray photon or charged particle detection system, comprising:
generating x-ray photons or charged particles of known energy;
converting particles into electron-hole pairs in a photoconductive detector;
reading out the photoconductive detector with a camera; and
processing images generated by the camera and tracking spots generated by the x-ray photons or charged particles received by the photoconductive detector and determining a relationship between the spots and the energy of the x-ray photons or charged particles.

16. The method of claim 15 employing a system comprising:
the photoconductive detector;
an optical microscope for reading out the photoconductive detector;
the camera coupled to the photoconductive detector by the optical microscope; and
a computer system that obtains images generated by the camera and tracks the response of the photoconductive detector to x-ray photons and/or charged particles over time.

* * * * *